US007229806B2

(12) United States Patent
Ben-Bassat et al.

(10) Patent No.: US 7,229,806 B2
(45) Date of Patent: *Jun. 12, 2007

(54) MICROBIAL CONVERSION OF GLUCOSE TO PARA-HYDROXYSTYRENE

(75) Inventors: Arie Ben-Bassat, Newark, DE (US); Wei Wei Qi, Broomall, PA (US); Fateme Sima Sariaslani, Wilmington, DE (US); Xiao-Song Tang, Hockessin, DE (US); Todd M. Vannelli, Ithaca, NY (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 319 days.

This patent is subject to a terminal disclaimer.

(21) Appl. No.: 10/439,478

(22) Filed: May 16, 2003

(65) Prior Publication Data

US 2004/0018600 A1   Jan. 29, 2004

Related U.S. Application Data

(60) Provisional application No. 60/383,450, filed on May 23, 2002.

(51) Int. Cl.
*C12P 7/22* (2006.01)
*C12N 9/88* (2006.01)
*C12N 1/20* (2006.01)
*C12N 1/00* (2006.01)
*C12N 1/12* (2006.01)
*C12N 5/10* (2006.01)
*C12N 5/02* (2006.01)
*C12N 15/00* (2006.01)

(52) U.S. Cl. ............... 435/156; 435/232; 435/69.1; 435/320.1; 435/325; 435/252.3; 435/254.11; 435/254.2; 435/257.2; 435/410; 435/252.33; 435/252.32; 536/23.2; 530/350

(58) Field of Classification Search ........... 435/232, 435/156, 69.1, 320.1, 325, 252.3, 254.11, 435/254.2, 257.2, 410, 252.33, 252.32; 536/23.2; 530/350
See application file for complete search history.

(56) References Cited

U.S. PATENT DOCUMENTS 4,985,587 A * 1/1991 Watkins et al. ............... 560/25
6,368,837 B1 * 4/2002 Gatenby et al. ............. 435/146

FOREIGN PATENT DOCUMENTS

WO   WO 94/08036 A1   4/1994
WO   WO 02/10407 A1   2/2002

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Bayne et al., Decarboxylative Conversion of Hydroxycinnamic Acids to Hydroxystyrenes by Polyporous circinata, J. Gen. Microbiol. 95, pp. 188-190, 1976.
Harada et al., Some properties of *p*-coumarate decarboxylase from , J. Gen. Microbiol. 11, pp. 1258-1262, 1976.
Goodey et al., Genetic and Biochemical Analysis of the Ability of *Saccharomyces cerevisiae* to Decarboxylate Cinnamic Acids, J. Gen. Microbiol., vol. 128, pp. 2615-2620, 1982.
Finkle et al., Enzyme Reactions with Phenolic Compounds: Formation of Hydroxystyrenes through the Decarboxylation of 4-Hydroxycinnamic Acids by Aerobacter, J. Biol. Bhem. vol. 237, pp. 2926-2931.
Lindsay et al., Decarboxylation of Substituted Cinnamic Acids by Enterobacteria: the Influence on Beer Flavour, J. Appl. Bacteriol., vol. 39, pp. 181-187, 1975.
Hashidoko et al., Cloning of DNA Fragment Carrying the 4-Hydroxycinnamate Decarboxylase (pofK) Gene from *Klebsiella oxytoca*, and Its Constitutive Expression in *Escherichia coli* JM109 Cells, Biolsci. Biotech. Biochem., vol. 58(1), pp. 217-218, 1994.
Hashidoko et al., Stereochemically Specific Proton Transfer in Decarboxylation of 4-Hydroxycinnamic Acids by 4-Hydroxycinnamate Decarboxylase from *Klebsiella oxytoca*, Arch. Biochem. Biophys. vol. 359(2), pp. 225-230, 1998.
Moore et al., Plant-like biosynthetic pathways in bactria: from benzoic acid to chalcone, J. Nat. Prod., 2000. vol. 65, pp. 1956-1962.
Takemoteo et al., Synthesis of styrenes through the biocatalytic decarboxylation of trans-cinnamic acids by plant cell cultures, Chem. Pharm. Bull., May 2001, vol. 49, No. 5, pp. 639-641.
Hwang et al., Production of plant-specific flavanones by *Escherichia coli* containing an artificial gene cluster, Appl. Enviorn. Microbiol., May 2003, vol. 69, No. 5. pp. 2699-2706.
Hashidoko et al., Induction of 4-hydroxycinnamate decarboxylase in *Klebsiella oxytoca* cells exposed to substrates and non-substrate 4-hydroxycinnamate analogs, Biosci. Biotechnol. Biochem., 2001, vol. 65, No. 12, pp. 2604-2612.
Faulkner, James. D.B. et al., High-level expression of the phenylalanine ammonia lyase-encoding gene from *Rhodosporidium toruloides* in *Saccharomyces cerevisiae* and *Escherichia coli* using a bifunctional expression, systems Gene, 1994, 13-20, 143, Elsevier Science, B.V.

(Continued)

*Primary Examiner*—Delia M. Ramirez

(57) ABSTRACT

An in vivo method for the production of pHS via a recombinant host cell is disclosed. The host cell expresses at least one gene encoding a polypeptide having para-hydroxycinnamic acid decarboxylase activity in combination with either at least one gene encoding a polypeptide having tyrosine ammonia lyase activity or at least one gene encoding a polypeptide having phenylalanine ammonia lyase activity.

10 Claims, No Drawings

OTHER PUBLICATIONS

Clausen, Monika et al., PAD1 encodes phenylacrylic acid decarboxylase which confers resistance to cinnamic acid in *Saccharomyces cerevisiae*, Gene, 1994, 107-112, 142, Elsevier Science, B.V.

van Beek, Sylvie et al., Decarboxylation of Substituted Cinnamic Acids by Lactic Acid Bacteria Isolated during Malt Whisky Fermentation, Applied and Environmental Microbiology, Dec. 2000, 5322-5328, vol. 66, No. 12, American Society for Microbiology.

* cited by examiner

MICROBIAL CONVERSION OF GLUCOSE TO PARA-HYDROXYSTYRENE

This application claims the benefit of U.S. Provisional Application No. 60/383,450, filed May 23, 2002.

FIELD OF THE INVENTION

This invention relates to the field of molecular biology and microbiology. More specifically, this invention relates to a method for producing para-hydroxystyrene from a simple carbon source such as glucose.

BACKGROUND OF THE INVENTION

Para-hydroxystyrene (pHS) is a well-known compound having potential utility in a wide variety of industrial applications, including the production of resins, coatings and inks.

A number of methods for the chemical synthesis of pHS are known. For example, pHS may be produced from ethyl benzene in a five-step process (U.S. Pat. No. 4,503,271) or from para-hydroxyacetophenol in a two step process (U.S. Pat. No. 5,523,378). Although it is possible to generate pHS by these methods, they typically require strongly acidic or basic reaction conditions, high reaction temperature, and generate large amounts of unwanted byproducts. In addition, chemical methods require expensive starting materials, which raise the cost of producing pHS. Despite the wide variety of uses for pHS, an inexpensive source of the material has not been developed.

A number of microorganisms have been found to produce 4-hydroxystyrenes, including fungi (Bayne et al., *J. Gen. Microbiol.* 95, 188–190 (1976) and Harada et al., *J. Gen. Microbiol.* 11, 1258–1262 (1976)), yeast (Goodey et al., *J. Gen. Microbiol,* 128, 2615–620 (1982)), and both Gram-negative and Gram-positive bacteria (Finkle et al. *J. Biol. Chem.* 237, 2926–2931 (1962), and Lindsay et al., *J. Appl. Bacteriol.* 39, 181–187 (1975)). In each of the above cases carboxylic acids of the phenylpropanoid class are decarboxylated to produce the corresponding 4-hydroxystyrene.

A para-hydroxycinnamic acid decarboxylase activity converts para-hydroxycinnamic acid (pHCA) to pHS (Hashidoko et al., *Biosci. Biotech. Biochem.,* 58(1), 217–218, (1994)). Release of 4-hydroxystyrene was reported when a DNA fragment carrying the 4-hyroxycinnamate decarboxylase gene from *Klebsiella oxytoca* was consitutively expressed in *E. coli* JM109. The recombinant host cell did not contain any additional genes for the production of the para-hydroxycinnamic acid (pHCA), the expected pHS precursor.

Additionally, Hashidoko et al. demonstrated production of hydroxystyrene by decarboxylation of 4-hydroxycinnamic acids by hydroxycinnamate decarboxylase from *Klebsiella oxytoca* (*Arch. Biochem. Biophys.* (1998), 359(2), 225–230)). The in vitro biological method of Hashidoko et al. for the production of pHS is limited to very low titer from the expensive starting material, pHCA.

In light of the foregoing, it would be an advancement in the art to provide a method for the production pHS using inexpensive materials such as carbohydrates or sugars and to increase the efficiency of a process for production of pHS through the pHCA intermediate. It would be particularly advantageous if the method produced a high level of the desired product with limited by-products. Development of such a method will require the ability to manipulate the genetic machinery responsible for the conversion of carbohydrates such as glucose to pHCA and pHCA to pHS.

The above mentioned biological and chemical systems provide a number of pathways that may be useful in the production of pHS, however, the efficient production of this monomer has not been achieved. The problem to be overcome therefore is to design and implement a method for the efficient production of pHS from a biological source using an inexpensive substrate or fermentable carbon source. Applicants have solved the stated problem by engineering a microbial host to produce pHS by expressing foreign genes encoding phenylalanine ammonia lyase/tyrosine ammonia lyase (PAL/TAL) and para-hydroxycinnamic acid decarboxylase (PDC) activity.

SUMMARY OF THE INVENTION

The present invention comprises an in vivo method for the production of pHS via a recombinant host cell expressing at least one gene encoding a polypeptide having para-hydroxycinnamic acid decarboxylase activity in combination with either at least one gene encoding a polypeptide having tyrosine ammonia lyase activity or at least one gene encoding a polypeptide having phenylalanine ammonia lyase activity.

Accordingly the present invention provides a method for the production of para-hydroxystyrene comprising:
(i) contacting a recombinant host cell with a fermentable carbon substrate, said recombinant host comprising:
  a) at least one gene encoding a polypeptide having tyrosine ammonia lyase activity; and
  b) at least one gene encoding a polypeptide having para-hydroxycinnamic acid decarboxylase activity;
(ii) growing said recombinant cell for a time sufficient to produce para-hydroxystyrene; and
(iii) optionally recovering said para-hydroxystyrene.

Alternatively the invention provides a method for the production of para-hydroxystyrene comprising:
(i) contacting a recombinant host cell with a fermentable carbon substrate, said recombinant host comprising:
  a) at least one gene encoding a polypeptide having phenylalanine ammonia lyase activity; and
  b) at least one gene encoding a polypeptide having para-hydroxycinnamic acid decarboxylase activity;
(ii) growing said recombinant cell for a time sufficient to produce para-hydroxystyrene; and
(iii) optionally recovering said para-hydroxystyrene Additionally the invention provides a recombinant host cell comprising:
a) a gene encoding a polypeptide having a tyrosine ammonia lyase activity; and
b) a gene encoding a polypeptide having para-hydroxycinnamic acid decarboxylase activity.

In similar fashion the invention provides a recombinant host cell comprising:
a) a gene encoding a polypeptide having a phenylalanine ammonia lyase activity; and
b) a gene encoding a polypeptide having a para-hydroxycinnamic acid decarboxylase activity.

BRIEF DESCRIPTION OF THE SEQUENCE LISTING

The following sequences conform with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions).

SEQ ID NO:1 is the nucleotide sequence of a phenylalanine-tyrosine ammonia lyase (pal/tal) enzyme from *R. glutinis*.

SEQ ID NO:2 is the deduced amino acid sequence of SEQ ID NO:1.

SEQ ID NO:3 is the nucleotide sequence of para-hydroxycinnamic acid decarboxylase (pdc1) from *L. plantarum*.

SEQ ID NO:4 is the deduced amino acid sequence of SEQ ID NO:3.

SEQ ID NO:5 is the nucleotide sequence of para-hydroxycinnamic acid decarboxylase (pdc2) from *B. subtilis*.

SEQ ID NO:6 is the deduced amino acid sequence of SEQ ID NO:5.

SEQ ID NO:7 is a primer used to amplify pal from *R. glutinis*.

SEQ ID NO:8 is a primer used to amplify pal from *R. glutinis*.

SEQ ID NO:9 is a primer used to amplify pdc1 from *L. plantarum*.

SEQ ID NO:10 is a primer used to amplify pdc1 from *L. plantarum*.

SEQ ID NO:11 is a primer used to amplify pdc2 from *B. subtilis*.

SEQ ID NO:12 is a primer used to amplify pdc2 from *B. subtilis*.

SEQ ID NO:13 is the amino acid sequence of a mutant TAL enzyme.

SEQ ID NO:14 is the amino acid sequence of the mutant TAL enzyme identified as RM120-1.

SEQ ID NO:15 is the amino acid sequence of the mutant TAL enzyme identified as RM120-2.

SEQ ID NO:16 is the amino acid sequence of the mutant TAL enzyme identified as RM120-4.

SEQ ID NO:17 is the amino acid sequence of the mutant TAL enzyme identified as RM120-7.

SEQ ID NO:18 is the amino acid sequence of the mutant TAL enzyme identified as RM492-1.

DETAILED DESCRIPTION OF THE INVENTION

The following abbreviations and definitions will be used for the interpretation of the specification and the claims.

"Phenylalanine ammonia-lyase" is abbreviated PAL.
"Tyrosine ammonia-lyase" is abbreviated TAL.
"para-Hydroxycinnamic acid" is abbreviated PHCA.
"Cinnamate 4-hydroxylase" is abbreviated C4H.
"para-Hydroxystyrene" is abbreviated pHS.
"para-hydroxycinnamic acid decarboxylase is abbreviated PDC.

As used herein the terms "cinnamic acid" and "cinnamate" are used interchangeably and are abbreviated CA.

The term "TAL activity" refers to the ability of a protein to catalyze the direct conversion of tyrosine to pHCA.

The term "PAL activity" refers to the ability of a protein to catalyze the conversion of phenylalanine to cinnamic acid.

The term "P-450/P-450 reductase system" refers to a protein system responsible for the catalytic conversion of cinnamic acid to pHCA. The P-450/P-450 reductase system is one of several enzymes or enzyme systems known in the art that perform a cinnamate 4-hydroxylase function. As used herein the term "cinnamate 4-hydroxylase" will refer to the general enzymatic activity that results in the conversion of cinnamic acid to PHCA, whereas the term "P-450/P-450 reductase system" will refer to a specific binary protein system that has cinnamate 4-hydroxylase activity.

The term "C4H" refers to Cinnamate 4-hydroxylase which is equivalent to the P-450 enzyme of the p450/p450 reductase system, required for hydroxylation of cinnamate.

The term "PAL/TAL activity" or "PAL/TAL enzyme" refers to a protein which contains both PAL and TAL activity. Such a protein has at least some specificity for both tyrosine and phenylalanine as an enzymatic substrate.

The term "mutant PAL/TAL" refers to a protein which has been derived from a wild type PAL enzyme which has greater TAL activity than PAL activity. As such, a mutant PAL/TAL protein has a greater substrate specificity for tyrosine than for phenylalanine.

The term "phenylalanine over-producing strain" refers to a microbial strain that produces endogenous levels of phenylalanine significantly higher than those seen in the wild-type of that strain. One specific example of an *E. coli* phenylalanine over-producer is the *E. coli* strain NST74 (U.S. Pat. No. 4,681,852). Others may include *Corynebacterium glutamicum* (Ikeda, M. and Katsumata, R. Metabolic engineering to produce tyrosine or phenylalanine in a tryptophan-producing *Corynebacterium glutamicum* strain, *Appl. Environ. Microbiol.* (1992), 58(3), pp. 781–785).

The term "tyrosine over-producing strain" refers to a microbial strain that produces endogenous levels of tyrosine significantly higher than those seen in the wildtype of that strain. One specific example of a tyrosine over-producer is the TI strain from Omnigene Bioproducts, Inc. (Cambridge, Mass.). Others may include *Corynebacterium glutamicum* (Masato, I. and Ryoichi, K. Metabolic engineering to produce tyrosine or phenylalanine in a tryptophan-producing *Corynebacterium glutamicum* strain, *Appl. Environ. Microbiol.* (1992), 58(3), pp. 781–785; Hagino, H. and Nakayama, K. Production of aromatic amino acids by microorganisms, *Agr. Biol. Chem.* (1973), 37(9), pp. 2001–2005 and 2013–2023) and *Brevibacterium lactofermentum* (Ito, H., Sakurai, S., Tanaka, T., Sato, K., Enei, H. Genetic breeding of L-tyrosine producer from *Brevibacterium lactofermentum, Agr. Biol. Chem.* (1990), 54(3), pp. 699–705).

The term "catalytic efficiency" will be defined as the $K_{cat}/K_M$ of an enzyme. "Catalytic efficiency" will be used to quantitate the specificity of an enzyme for a substrate.

The term "$K_{cat}$" is often called the "turnover number". The term "$K_{cat}$" is defined as the maximum number of substrate molecules converted to products per active site per unit time, or the number of times the enzyme turns over per unit time. $K_{cat}=Vmax/[E]$, where [E] is the enzyme concentration (Ferst, In *Enzyme Structure and Mechanism*, $2^{nd}$ ed.; W. H. Freeman: New York, 1985; pp. 98–120).

The term "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

"Gene" refers to a nucleic acid fragment that expresses a specific protein, including regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

"Coding sequence" refers to a DNA sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell.

"Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used here are well known in the art and are described by Sambrook, J., Fritsch, E. F. and Maniatis, T. *Molecular Cloning: A Laboratory Manual*, $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions;* Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

The present invention describes biological methods for the production of para-hydroxystyrene (pHS). These methods make use of genes encoding proteins phenylalanine ammonia-lyase (PAL) activity or tyrosine ammonia-lyase (TAL) activity and para-hydroxycinnamic acid decarboxylase (PDC) activity. A PAL activity will convert phenylalanine to pHCA in the presence of a P-450/P-450 reductase [cinnamate-4-hydroxylase (C4H) and P-450 reductase] system. An enzyme having a high TAL activity will convert tyrosine directly to pHCA without any intermediate steps. para-Hydroxycinnamic acid decarboxylase is known to decarboxylate PHCA to pHS.

Accordingly a microbial host may be engineered to produce pHS either by the introduction of at least one gene encoding PDC, in combination with either a gene encoding PAL and P-450/P-450 reductase system, or with a gene encoding a TAL activity.

The present invention provides an inexpensive biological route to pHS which is useful in a variety of commercial materials including ion exchange resins, binder resin for inks, polymer blend compatibilizers, permselective membranes, and polymer supports. Additionally, pHS may also be used in various coatings applications such as UV curable coatings, metal surface treatments and high temperature hot melt adhesion applications.

Genes

The key enzymatic activities used in the present invention are encoded by a number of genes known in the art. The principal enzyme activities include phenylalanine ammonium lyase (PAL), tyrosine ammonium lyase (TAL) and para-hydroxycinnamic acid decarboxylase (PDC). Where it is desired to use a PAL enzyme in a recombinant host it may additionally be necessary to obtain and express genes encoding either a cinnamate-4-hydroxylase (C4H) or a P-450/P-450 reductase system.

Phenylalanine Ammonium Lyase (PAL), Tyrosine Ammonium Lyase (TAL) and Para-hydroxycinnamic Acid Decarboxylase (PDC) Activities.

Genes encoding PAL are known in the art and several have been sequenced from both plant and microbial sources (see for example EP 321488 *[R. toruloides];* WO 9811205 *[Eucalyptus grandis* and *Pinus radiata];* WO 9732023 [Petunia]; JP 05153978 *[Pisum sativum];* WO 9307279 [potato, rice]). The sequence of PAL genes is available (see for example GenBank AJ010143 and X75967). Where expression of a wild type PAL gene in a recombinant host is desired the wild type gene may be obtained from any source including but not limited to, yeasts such as *Rhodotorula* sp., *Rhodosporidium* sp. and *Sporobolomyces* sp.; bacterial organisms such as *Streptomyces*; and plants such as pea, potato, rice, eucalyptus, pine, corn, petunia, arabidopsis, tobacco, and parsley.

There are no known genes which encode an enzyme having exclusively TAL activity, i.e., which will use only tyrosine as a substrate for the production of pHCA. However several of the PAL enzymes mentioned above have some substrate affinity for tyrosine, and a recently described enzyme from *Rhodobacter capsulatus* has a catalytic efficiency for tyrosine that is approximately 150-fold greater than that for phenylalanine (Kyndt et al., *FEBS Lett.* 512: 240 (2002)). Thus genes encoding TAL activity may be identified and isolated concurrently with the pal genes described above. For example, the PAL enzyme isolated from parsley (Appert et al., *Eur. J. Biochem.* 225:491 (1994)) and corn ((Havir et al., *Plant Physiol.* 48:130 (1971)) both demonstrate the ability to use tyrosine as a substrate. Similarly, the PAL enzyme isolated from *Rhodosporidium* (Hodgins, D. S., *J. Biol. Chem.* 246:2977 (1971)) also may use tyrosine as a substrate. Such enzymes will be referred to herein as PAL/TAL enzymes or activities. Where it is desired to create a recombinant organism expressing a wild type gene encoding PAL/TAL activity, genes isolated from maize, wheat, parsley, *Rhizoctonia solani, Rhodosporidium, Sporobolomyces pararoseus* and *Rhodosporidium* may be used as discussed in Hanson and Havir, *The Biochemistry of Plants;* Academic: New York, 1981; Vol. 7, pp. 577–625, where the genes from *Rhodosporidium* are preferred.

Genes encoding para-hydroxycinnamic acid decarboxylase (PDC) are known, and any one may be suitable in the present invention. For example, genes encoding PDC have been isolated from *Lactobacillus plantarum* (AAC45282.1 GI:1762616); *Lactobacillus crispatus* (AAF82761.1 GI:9082168); *Lactobacillus paracasei* (AAF82762.1 GI:9082170); *Lactobacillus pentosus* (AAF82763.1 GI:9082172) *Lactobacillus brevis* (AAF82766.1 GI:9082178) *Lactobacillus sakei* (AA85433.1 GI:15150391) *Pediococcus pentosaceus.* (CAC 16794.1 GI: 11322458); *Bacillus pumilus* (CAC18719.1 GI: 11691810); and *Lactococcus lactis* (NP_268087.1 GI:15673912), where the PDC gene isolated from *Lactobacillus plantarum* and *Bacillus subtilis* encoding the polypeptides as set forth in SEQ ID NO: 4 and SEQ ID NO: 6 respectively are preferred.

Where PAL is chosen as the principal enzyme for the conversion of phenylalanine to PHCA, it may be necessary to clone the genes encoding polypeptides having the cinnamate-4-hydroxylase and the P-450 reductase activities. Where it is desired to express the P-450/P-450 reductase system, the genetic elements of this system are known and available in the art. For example, the reductase has been isolated from Jerusalem Artichoke (*Helianthus tuberosus*), [embl locus HTU2NFR, accession Z26250.1]; parsley, (*Petroselinum crispum*) [Koopmann et al., *Proc. Natl. Acad. Sci. U.S.A.* 94 (26), 14954–14959 (1997), [locus AF024634 accession AF024634.1]; California poppy (*Eschscholzia californica*), Rosco et al., *Arch. Biochem. Biophys.* 348 (2), 369–377 (1997), [locus ECU67186 accession U67186.1]; *Arabidopsis thaliana*, [pir: locus S21531]; spring vetch (*Vicia sativa*), [pir: locus S37159]; mung bean, (*Vigna radiata*), Shet et al., *Proc. Natl. Acad. Sci. U.S.A.* 90 (7), 2890–2894 (1993), [pir: locus A47298]; and opium poppy (*Papaver somniferum*), [locus PSU67185 accession U67185.1].

The cytochrome P-450 has been isolated from the Jerusalem Artichoke (*Helianthus tuberosus*),[embl locus HTTC4MMR, accession Z17369.1]; *Zinnia elegans,* [swissprot: locus TCMO_ZINEL, accession Q43240] *Catharanthus roseus* [swissprot: locus TCMO_CATRO, accession P48522]; *Populus tremuloides* [swissprot: locus TCMO_POPTM, accession O24312];*Populus kitakamiensis* [swissprot: locus TCMO_POPKI, accession Q43054]; *Glycyrrhiza echinata* [swissprot: locus TCMO_GLYEC, accession Q96423]; *Glycine max* [swissprot: locus TCMO_SOYBN, accession Q42797] as well as other sources.

Genes encoding cinnamate-4-hydroxylase (C4H) are also known and have been isolated from a variety of plant sources including, *Lithospermum* (Genbank AB055508; Genbank AB055508), *Gossypium* (Genbank AF286648), *Capsicum* (Genbank AF212318), *Catharanthus* (Swissprot P48522), *Populus* (Genbank AF302495; Swissprot Q43054), Helianthus (Swiss prot Q04468) *Zinnia,* (Swissprot Q43240) and *Citrus* (Genbank AF255014).

It will be appreciated that the present invention is not limited to the genes encoding polypeptides having the specific activities mentioned above, but will encompass any suitable homologs of such genes that may be obtained by standard methods. Methods of obtaining homologs to these genes using sequence-dependant protocols are well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction (PCR), ligase chain reaction (LCR)).

For example, genes encoding homologs of anyone of the polypeptides having the above mentioned activities could be isolated directly by using all or a portion of the known sequences as DNA hybridization probes to screen libraries from any desired plant, fungi, yeast, or bacteria using methodology well known to those skilled in the art. Specific oligonucleotide probes based upon the literature nucleic acid sequences can be designed and synthesized by methods known in the art (Maniatis, supra). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full-length cDNA or genomic fragments under conditions of appropriate stringency.

In addition, two short segments of the literature sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the literature sequences, and the sequence of the other primer takes advantage of the presence of the polyadenylic acid tracts to the 3' end of the mRNA precursor encoding bacterial genes. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the literature sequences. Using commercially available 3' RACE or 5' RACE systems (GIBCO BRL, Rockville, Md.), specific 3' or 5' cDNA fragments can be isolated (Ohara et al., *Proc. Natl. Acad. Sci. USA* 86:5673 (1989); Loh et al., *Science* 243:217 (1989))

Mutant PAL/TAL Activities:

Where conversion of Tyosine directly to PHCA is desired it will be beneficial to derive mutants expressing a mutant PAL/TAL activity having a greater substrate specificity for tyrosine than for phenylalanine. A variety of methods are available to produce such mutants. Typically the approach will involve the selection of an organism having a PAL/TAL activity with a higher substrate specificity for tyrosine than for phenylalanine. Generally, the substrate specificity is quantitated by $K_{cat}/K_M$ (catalytic efficiency), calculated on the basis of the number of active sites identified in the enzyme.

Phenylalanine ammonia-lyase has a molecular weight of about 330,000 and consists of four identical subunits of about 80 kDa (Havir et al., *Biochemistry* 14:1620–1626 (1975)). It has been suggested that PAL contains a catalytically essential dehydroalanine residue (Hanson et al., *Arch. Biochem. Biophys.* 141:1–17 (1970)). Ser-202 of PAL from parsley has been indicated as the precursor of the dehydroalanine (Langer et al., *Biochemistry*, 36:10867–10871 (1997)). The $K_{cat}$ for PAL was calculated using information available from recent studies on the crystal structure of a homologous enzyme, histidine ammonia-lyase (HAL). These studies have revealed that the reactive electrophilic residue in the active site of the enzyme is a 4-methylidene-ididazole-5-one, which is autocatalytically formed by cyclization and dehydration of residues 142–144 containing the Ala-Ser-Gly sequence (Schwede et al., *Biochemistry* 38:5355–5361 (1999)). Since all tetrameric PAL enzymes studied so far, also contain the Ala-Ser-Gly sequence at each of their active sites, it is likely that each active site of PAL also contains a 4-methylidene-ididazole-5-one formed from this sequence.

Within the context of the present invention, the suitable wildtype enzyme selected for mutagenesis has a catalytic efficiency of about $4.14 \times 10^3$ to $1 \times 10^9$ $M^{-1} sec^{-1}$ for tyrosine where a catalytic efficiency in a range of about $1 \times 10^4$ $M^{-1} sec^{-1}$ to about $5 \times 10^4$ $M^{-1} sec^{-1}$ is preferred.

The process of the selection of a suitable PAL/TAL enzyme, involves construction of a weak expression vector, mutagenesis and evolution of the pal coding sequence, and finally selection of variants with improved TAL activity.

Mutagenesis of Pal:

A variety of approaches may be used for the mutagenesis of the PAL/TAL enzyme. Two suitable approaches used herein include error-prone PCR (Leung et al., *Techniques*, 1:11–15 (1989) and Zhou et al., *Nucleic Acids Res.* 19:6052–6052 (1991) and Spee et al., *Nucleic Acids Res.* 21:777–778 (1993)) and in vivo mutagenesis.

The principal advantage of error-prone PCR is that all mutations introduced by this method will be within the pal gene, and any change may be easily controlled by changing the PCR conditions. Alternatively in vivo mutagenesis, may be employed using commercially available materials such as *E. coli* XL1-Red strain, and the *Epicurian coli* XL1-Red mutator strain from Stratagene (Stratagene, La Jolla, Calif., Greener and Callahan, *Strategies* 7:32–34 (1994)). This strain is deficient in three of the primary DNA repair pathways (mutS, mutD and mutT), resulting in a mutation rate 5000-fold higher than that of wild type. In vivo mutagenesis does not depend on ligation efficiency (as with error-prone PCR), however a mutation may occur at any region of the vector and the mutation rates are generally much lower.

Irrespective of the method of mutagenesis it is contemplated that an enzyme may be evolved having a catalytic efficiency of about $4.14 \times 10^3$ $M^{-1} sec^{-1}$ to about $1 \times 10^9$ $M^{-1} sec^{-1}$ where a catalytic efficiency of about $12.6 \times 10^3$ $M^{-1} sec^{-1}$ is typical.

Selection of Variants with Improved TAL Activity:

Selection via Reversibility of Tyrosine to pHCA Reaction

In order to select for those mutants having genes encoding proteins with enhanced TAL activity, a selection system based on the reversibility of the tyrosine to PHCA reaction was developed. It will be appreciated that the TAL activity responsible for the conversion of tyrosine to pHCA is in a state of equilibrium with the opposite reaction. Mutant genes were cloned by standard methods into *E. coli* tyrosine auxotrophs, unable to grow in the absence of tyrosine. Transformants were plated on tyrosine minus medium in the presence of suitable concentrations of pHCA. Those colonies which grew under these conditions were picked and analyzed for the presence of the mutant gene. In this fashion, a gene was isolated that expressed an enzyme having a catalytic efficiency of about $12.6 \times 10^3$ $M^{-1} sec^{-1}$ and a ratio of TAL catalytic activity to PAL catalytic activity of 1.7 compared to 0.5 for the wild type.

The skilled person will be able to envision additional screens for the selection of genes encoding enhanced TAL activity. For example, it is well known that *Acinetobacter calcoaceticus* DSM 586 (ATCC 33304) is able to efficiently degrade p-coumaric acid (PHCA) and use it as a sole carbon source (Delneri et al., *Biochim. Biophys. Acta* 1244:363–367 (1995)).

Selection via Comparison of TAL/PAL Ratio

The skilled artisan will appreciate that development of a high throughput assay for the identification of genes possessing altered PAL or TAL activity would greatly facilitate screening of microbial transformants. A simple method is disclosed that relies on separate measurements of the TAL and PAL activities in whole cells. The ratio of TAL to PAL activity then may be calculated and quickly compared to wild type activity, to monitor changes in the bio-catalyst activity.

Identification of Critical Amino Acids for TAL Activity

Using the above approach Applicants have identified a variety of mutant PAL enzymes that have increased TAL activity, compared to the wild type gene. These mutants were identified using the methods of mutagenesis and screening described above. The mutants, the altered amino acid residues, and the TAL/PAL activity are summarized below.

| Strain | Mutations | TAL/PAL ratio |
|---|---|---|
| Wild Type PAL | None | 0.5 |
| EP18Km-6 (mutant PAL) | CTG(Leu215) to CTC(Leu) | 1.7 |
|  | GAA(Glu264) to GAG(Glu) |  |
|  | GCT(Ala286) to GCA(Ala) |  |
|  | ATC(Ile540) to ACC(Thr) |  |
| RM120-1 | GAC(Asp126) to GGC(Gly) | 7.2 |
|  | CAG(Gln138) to CTG(Leu) |  |
|  | CTG(Leu215) to CTC(Leu) |  |
|  | GAA(Glu264) to GAG(Glu) |  |
|  | GCT(Ala286) to GCA(Ala) |  |
|  | ATC(Ile540) to ACC(Thr) |  |
| RM120-2 | TTG(Leu176) to CTG(Leu) | 2.1 |
|  | GGC(Gly198) to CAC(Asp) |  |
|  | CTG(Leu215) to CTC(Leu) |  |
|  | GAA(Glu264) to GAG(Glu) |  |
|  | GCT(Ala286) to GCA(Ala) |  |
|  | ATC(Ile540) to ACC(Thr) |  |
| RM120-4 | TCG(Ser181) to CCG(Pro) | 2.0 |
|  | GTC(Val235) to GCC(Ala) |  |
|  | CTG(Leu215) to CTC(Leu) |  |
|  | GAA(Glu264) to GAG(Glu) |  |
|  | GCT(Ala286) to GCA(Ala) |  |
|  | ATC(Ile540) to ACC(Thr) |  |
| RM120-7 | TCG(Ser149) to CCG(Pro) | 0.8 |
|  | ATC(Ile202) to GTC(Val) |  |
|  | CTG(Leu215) to CTC(Leu) |  |
|  | GAA(Glu264) to GAG(Glu) |  |
|  | GCT(Ala286) to GCA(Ala) |  |
|  | ATC(Ile540) to ACC(Thr) |  |
| RM492-1 | GTC(Val502) to GGC(Gly) | 2.0 |
|  | CTG(Leu215) to CTC(Leu) |  |
|  | GAA(Glu264) to GAG(Glu) |  |
|  | GCT(Ala286) to GCA(Ala) |  |
|  | ATC(Ile540) to ACC(Thr) |  |

It will be appreciated that the invention encompasses, not only the specific mutations described above, but also those that allow for the substitution of chemically equivalent amino acids. So for example where a substitution of an amino acid with the aliphatic, nonpolar amino acid alanine is made, it will be expected that the same site may be substituted with the chemically equivalent amino acid serine. Thus the invention provides mutant TAL proteins having the following amino acid substitutions within the wildtype TAL amino acid sequence (SEQ ID NO:24):

| Sequence ID No. | Position | WT Amino Acid | Possible Amino Acids |
|---|---|---|---|
| 13 | 126 | Asp | Gly, Ala, Ser, Thr |
|  | 138 | Gln | Leu, Met, Ile, Val, Cys |
|  | 149 | Ser | Pro, Ala, Ser, Thr, Gly |
|  | 181 | Ser | Pro, Ala, Ser, Thr, Gly |
|  | 198 | Gly | Asp, Asn, Glu, Gln |
|  | 202 | Ile | Val, Met, Leu, Cys |
|  | 235 | Val | Ala, Gly, Ser, Thr, Pro |
|  | 502 | Val | Gly, Ala, Ser, Thr, Pro |
|  | 540 | Ile | Thr, Ala, Ser, Pro, Gly |
| 14 | 126 | Asp | Gly, Ala, Ser, Thr |
|  | 138 | Gln | Leu, Met, Ile, Val, Cys |
|  | 540 | Ile | Thr, Ala, Ser, Pro, Gly |
| 15 | 198 | Gly | Asp, Asn, Glu, Gln |
|  | 540 | Ile | Thr, Ala, Ser, Pro, Gly |
| 16 | 181 | Ser | Pro, Ala, Ser, Thr, Gly |
|  | 235 | Val | Ala, Gly, Ser, Thr, Pro |
|  | 540 | Ile | Thr, Ala, Ser, Pro, Gly |
| 17 | 149 | Ser | Pro, Ala, Ser, Thr, Gly |
|  | 202 | Ile | Val, Met, Leu, Cys |
|  | 540 | Ile | Thr, Ala, Ser, Pro, Gly |
| 18 | 502 | Val | Gly, Ala, Ser, Thr, Pro |
|  | 540 | Ile | Thr, Ala, Ser, Pro, Gly |

Reproduction Production—Microbial Hosts:

The production organisms of the present invention will include any organism capable of expressing the genes required for the pHCA production. Typically the production organism will be restricted to microorganisms and plants.

Microorganisms useful in the present invention for the production of pHS may include, but are not limited to bacteria, such as the enteric bacteria (*Escherichia*, and *Salmonella* for example) as well as *Bacillus, Acinetobacter, Actinomycetes* such as *Streptomyces, Corynebacterium, Methanotrophs* such as *Methylosinus, Methylomonas, Rhodococcus* and *Pseudomona; Cyanobacteria*, such as *Rhodobacterand Synechocystis;* yeasts, such as *Saccharomyces, Zygosaccharomyces, Kluyveromyces, Candida, Hansenula, Debaryomyces, Mucor, Pichia* and *Torulopsis;* and filamentous fungi such as *Aspergillus* and *Arthrobotrys*, and algae for example. The pal, pal/tal, C4H and pdc genes of the present invention may be produced in these and other microbial hosts to prepare large, commercially useful amounts of pHS.

Although any of the above mentioned microorganisms would be useful in the production of pHS, preferred are mutant strains of bacteria that over produce either phenylalanine or tyrosine. The present invention provides methods for the production of pHS using at least two different combinations of genetic elements. In one case a recombinant host may be constructed such that it expresses at least one gene encoding a polypeptide having tyrosine ammonia lyase activity and at least one gene encoding a polypeptide having para-hydroxycinnamic acid decarboxylase activity. In this situation it is preferred if the recombinant host over-express tyrosine. Tyrosine overproducing strains are known and include, but are not limited to *Corynebacteria, Brevibacteria, Microbacterium, E. coli, Arthrobacter, Candida, Citrobacter, Pseudomonas* and *Methylomonas*. Particularly useful tyrosine overproducing strains include but are not limited to *Microbacterium ammoniaphilum* ATCC 10155, *Corynebactrium lillium* NRRL-B-2243, *Brevibacterium divaricatum* NRRL-B-2311, *Arthrobacter citreus* ATCC 11624, and *Methylomonas* SD-20. Other suitable tyrosine overproducers are known in the art, see for example *Microbial production of L-tyrosine: A Review*, T. K. Maiti et al, Hindustan Antibiotic Bulletin, vol 37, 51–65, 1995.

Alternatively, the recombinant host may include at least one gene encoding a polypeptide having phenylalanine ammonia lyase activity in combination with at least one gene encoding a polypeptide having para-hydroxycinnamic acid decarboxylase activity. In this situation it is additionally necessary that the cell also express some set of genes having cinnamate 4-hydroxylase, (P-450/P-450 reductase) system as discussed above. These supplemental genes may be native to the host cell or may be introduced. In either case, where the principal enzyme has a substrate preference for phenylalanine as opposed to tyrosine, it is preferred if the host cell be a phenylalanine overproducer. Phenylalanine overproducing strains are known and include but are not limited to *E. coli, Microbacterium Corynebacteria, Arthrobacter, Pseudomonas* and *Brevibacteria*. Particularly useful phenylalanine overproducing strains include, but are not limited to *Microbacterium ammoniaphilum* ATCC 10155, *Corynebactrium lillium* NRRL-B-2243, *Brevibacterium divaricatum* NRRL-B-2311, *E. coli* NST74 and *Arthrobacter citreus* ATCC 11624. Other suitable phenylalanine overproducing strains are known and a review may be found in Maiti et al, Supra and *Metabolic Engineering For Microbial Production Of Aromatic Amino Acids And Derived Compounds*, J. Bongaertes et al, *Metabolic Engineering* vol 3, 289–300, 2001.

Microbial expression systems and expression vectors containing regulatory sequences that direct high level expression of foreign proteins are well known to those skilled in the art. Any of these could be used to construct chimeric genes for production of pHS. These chimeric genes could then be introduced into appropriate microorganisms via transformation to allow for expression of high level of the enzymes.

Vectors or cassettes useful for the transformation of suitable microbial host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the relevant genes in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, trp, $IP_L$, $IP_R$, T7, tac, and trc (useful for expression in *Escherichia coli*).

Termination control regions may also be derived from various genes native to the preferred hosts. Optionally, a termination site may be unnecessary, however, it is most preferred if included.

Where commercial production of pHS is desired a variety of fermentation methodologies may be applied. For example, large scale production may be effected by both batch or continuous fermentation.

A classical batch fermentation is a closed system where the composition of the media is set at the beginning of the fermentation and not subject to artificial alterations during the fermentation. Thus, at the beginning of the fermentation the medium is inoculated with the desired microorganism or microorganisms and fermentation is permitted to occur adding nothing to the system. Typically, however, the concentration of the carbon source in a "batch" fermentation is limited and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in the log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the medium. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, T. D.; *Biotechnology: A Textbook of Industrial Microbiology*, 2nd ed.; Sinauer Associates: Sunderland, Mass., 1989; or Deshpande, M. V. *Appl. Biochem. Biotechnol.* 36:227, (1992), herein incorporated by reference.

Commercial production of pHS may also be accomplished with continuous fermentation. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in their log phase of growth.

Continuous fermentation allows for modulation of any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by the medium turbidity, is kept constant. Continuous systems strive to maintain steady state growth conditions and thus the cell loss due to the medium removal must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

Recombinant Production—Plants:

Plants and algae are also known to possess a complete and complex phenylpropenoid pathway involving many of the enzymes needed for the production of pHS according to the present invention. The nucleic acid fragments of the instant invention may be used to create transgenic plants having the ability to express the necessary genes for the production of pHS. Preferred plant hosts will be any variety that will support a high production level of the instant enzymes. Suitable green plants will include but are not limited to soybean, rapeseed (*Brassica napus, B. campestris*), sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa*, L), sorghum (*Sorghum bicolor*), rice (*Oryza sativa*), *Arabidopsis*, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include but not limited to commercially significant hosts such as *Spirulina, Haemotacoccus*, and *Dunalliela*. Overproduction of pHS may be accomplished by first constructing chimeric genes of present invention in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequences of the present invention should be capable of promoting expression of the present gene product. High level plant promoters that may be used in this invention include the promoter of the small subunit (ss) of the ribulose-1,5-bisphosphate carboxylase from example from soybean (Berry-Lowe et al., *J. Molecular and App. Gen.*, 1:483–498 (1982)), and the promoter of the chlorophyll a/b binding protein. These two promoters are known to be light-induced in plant cells (see, for example, *Genetic Engineering of Plants, an Agricultural Perspective*, A. Cashmore, Plenum, N.Y. (1983), pages 29–38; Coruzzi, G. et al., *The Journal of Biological Chemistry,* 258:1399 (1983), and Dunsmuir, P. et al., *Journal of Molecular and Applied Genetics,* 2:285 (1983)).

Plasmid vectors comprising the instant chimeric genes can then be constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.* 4:2411–2418 (1985); De Almeida et al., *Mol. Gen. Genetics* 218:78–86 (1989)), and thus that multiple events must be screened in order to obtain lines displaying the desired expression level and pattern. Such screening may be accomplished by Southern analysis of DNA blots (Southern, *J. Mol. Biol.* 98, 503, (1975)). Northern analysis of mRNA expression (Kroczek, *J. Chromatogr. Biomed. Appl.,* 618 (1–2):133–145 (1993)), Western analysis of protein expression, or phenotypic analysis.

It is contemplated that it will be possible to create mutants of the various elements of the enzymatic pathway for pHS production that will result in higher levels of intra or extra cellular pHS accumulation. Various methods are known for mutating a native gene sequence to produce a gene product with altered or enhanced activity including but not limited to error prone PCR (Melnikov et al., *Nucleic Acids Research,* (Feb. 15, 1999) Vol. 27, No. 4, pp. 1056–1062); site directed mutagenesis (Coombs et al., *Proteins* (1998), 259–311, 1 plate. Editor(s): Angeletti, Ruth Hogue. Publisher: Academic, San Diego, Calif.) and "gene shuffling" (U.S. Pat. No. 5,605,793; U.S. Pat. No. 5,811,238; U.S. Pat. No. 5,830,721; and U.S. Pat. No. 5,837,458, incorporated herein by reference).

Description of the Preferred Embodiments:

The method of production defined in this invention involves incorporation of pal/tal and pdc genes into a single host organism and conversion of renewable resources such as glucose to pHS.

To identify effective genes encoding para-hydroxycinnamic acid decarboxylase (pdc) cell extracts from a variety of microorganisms were screened. High levels of PDC were observed in *Lactobacillus plantarum* (ATCC#14917) and this strain was selected for further study. Additionally, a variety of microorganisms were examined for the ability to convert pHCA to pHS, on the assumption that these organisms may be expressing higher levels of a PDC enzyme. High conversion rates of pHCA to pHS were observed in *Bacillus subtilis* (ATCC#6633) and this strain was selected for further study. Using oligonucleotide primers designed from the known sequence of a Lactobacillus para-coumaric acid decarboxylase (GenBank Accession no. U63827), two pdc genes were isolated and designated pdc1 from *Lactobacillus plantarum* and pdc2 from *Bacillus subtilis*. The genes pdc1 and pdc2 were isolated and cloned into a phenylalanine overproducing strain, harboring a heterologous gene encoding a *Rhodotorula* phenylalanine ammonium lyase. Production of pHS was observed in good yields when cells were grown on a variety of fermentable carbon substrates.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Procedures required for PCR amplification, DNA modifications by endo- and exonucleases for generating desired ends for cloning of DNA, ligation, and bacterial transformation are well known in the art. Standard molecular cloning techniques used herein are well known in the art and are described by Sambrook, J., Fritsch, E. F. and Maniatis, T., *Molecular Cloning: A Laboratory Manual*, $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W., *Experiments with Gene Fusions;* Cold Spring Harbor Laboratory: Cold Spring, N.Y., 1984 and by Ausubel et al., *Current Protocols in Molecular Biology;* Greene Publishing and Wiley-Interscience; 1987.

Materials and methods suitable for the maintenance and growth of bacterial cultures are well known in the art. Techniques suitable for use in the following Examples may be found as set out in *Manual of Methods for General Bacteriology;* Phillipp Gerhardt, R. G. E. Murray, Ralph N. Costilow, Eugene W. Nester, Willis A. Wood, Noel R. Krieg and G. Briggs Phillips, Eds., American Society for Microbiology: Washington, D.C., 1994 or by Brock, T. D.; *Biotechnology: A Textbook of Industrial Microbiology,* 2nd ed.; Sinauer Associates: Sunderland, Mass., 1989. All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

PCR reactions were run on a GeneAMP PCR System 9700 using Amplitaq or Amplitaq Gold enzymes (PE Applied Biosystems, Foster City, Calif.). The cycling conditions and reactions were standardized according to the manufacture's instructions.

The meaning of abbreviations used is as follows: "sec" means second(s), "min" means minute(s), "h" means hour(s), "d" means day(s), "μL" means microliter, "mL" means milliliters, "L" means liters, "mm" means millimeters, "nm" means nanometers, "mM" means millimolar, "M" means molar, "mmol" means millimole(s), "μmole" mean micromole", "g" means gram, "μg" means microgram and "ng" means nanogram, "U" means units, "mU" means milliunits, "rpm" means revolutions per minute, "OD" means optical density, "HPLC" means high performance liquid chromatography, "IPTG" means isopropyl β-D-thiogalactopyranoside, "X-gal" means 5-bromo-4-chloro-3-indolyl-beta-D-galactopyranoside, and "g" is the gravitation constant.

General Methods:

Sample Preparation for HPLC Analysis:

An HPLC assay was developed for measuring the levels of cinnamic acid, pHCA, pHS, phenylalanine and tyrosine formed by the whole cells. In a typical assay, following centrifugation of a culture grown in the medium of choice, 200–1000 μL of the supernatant was acidified with phosphoric acid, filtered through a 0.2 or 0.45 micron filter and analyzed by HPLC to determine the concentration of pHS, pHCA, cinnamic acid, phenylalanine and tyrosine in the growth medium.

HPLC Method:

A Hewlett Packard 1090L HPLC system with an auto sampler and a diode array UV/Vis detector was used with a reverse-phase Zorbax SB-C8 column (4.6 mm×250 mm) supplied by MAC-MOD Analytical Inc. (Chadds Ford, Pa.). A flow rate of 1.0 mL per min, and a column temperature of 40° C. was used in the assay. The UV detector was set to monitor the eluant at 250, 230, 270, 290 and 310 nm wavelengths. The conditions used for the HPLC analysis are specified in Table 1. The retention time of metabolites subject to analysis using the conditions described in Table 1 are listed in Table 2.

TABLE 1

Solvents/Gradients

| Time (min) | Solvent A Methanol | Solvent B H2O + 0.2% TFA* |
|---|---|---|
| 0.0 | 10% | 90% |
| 0.1 | 10% | 90% |
| 9.0 | 35% | 65% |
| 9.1 | 50% | 50% |
| 14.0 | 50% | 50% |
| 18.0 | 100% | 0% |
| 21.0 | 100% | 0% |

*TFA = trifluoroacetic acid

TABLE 2

Retention Time of Metabolites Subject to Analysis

| Compounds (1.0 mM) | Retention Time (min) |
|---|---|
| tyrosine | 6.7 |
| phenylalanine | 9.4 |
| 4-hydroxybenzoic acid (pHBA) | 11.6 |
| 3,4-dihydroxycinnamate (caffeic acid) | 12.5 |
| 3-(4-hydroxyphenyl)propionate | 13.3 |
| 4-hydroxyphenylpyruvate | 13.6 |
| 4-hydroxyacetaphenone | 14.0 |
| 4-hydroxycinnamic acid (pHCA) | 14.2 |
| 2-hydroxycinnamic acid (oHCA) | 15.3 |
| benzoic acid | 15.5 |
| coumarin | 16.0 |
| para-hydroxystyrene (pHS) | 16.6 |
| cinnamyl alcohol | 17.3 |
| phenylpyruvate | 18.1 |
| cinnamic acid (CA) | 18.3 |

Example 1

Screening of PDC Activity in Cell-Free Extracts

The purpose of this Example was to screen a number of bacterial and yeast strains for PDC enzyme activity, cell growth and pHCA induction.

The following strains were streaked out from glycerol stock onto LB plates: *Bacillus subtilis* (ATCC#6633), *Pseudomonas fluorescens* (ATCC#11156), *Pseudomonas fluorescens* (ATCC#17559), and *Pseudomonas putida* Type A (ATCC#17453). *Lactobacillus plantarum* (ATCC#14917) and *Rhodotorula rubra* (ATCC#889) were streaked out on nutrient agar plates. All these strains were grown at either 37° C. or 30° C. Single colonies were then selected and transferred to 50 mL of the liquid media, either LB, MRS (Difco), or 2×YT in 250 mL sterile flasks. The cells were grown overnight at 37° C. or 30° C. on a shaker at 250 rpm. A 5.0 mL aliquot from each strain was then transferred into two 250 mL flasks containing 45 mL of fresh medium. To one of the flasks containing *B. subtilis, P. fluorescens, S. cerevisiae* (ATCC#2034), or *Rhodotorula rubra* (ATCC#889), pHCA was added to a final concentration of 1.2 mM. These cells were then allowed to grow to saturation before they were harvested by centrifugation. To one of the flasks containing the *L. plantarum* strain, pHCA was added to a final concentration of 1.2 mM after the culture reached mid-log phase and the cells were harvested after 1.0 h.

Preparation of Cell Free Extracts:

The cells were washed and then resuspended in 25 mM phosphate buffer, pH 6.0, containing leupeptin, pepstatin A, and E-64 (protease inhibitor, Roche Molecular Biochemicals, Indianapolis, Ind.) at 1.0 µg/mL, bestatin at 40 µg/mL, EDTA at 1.0 mM, and 4-(2-aminoethyl) benzenesulfonyl fluoride hydrochloride (AEBSF, obtained from Aldrich) at 0.1 mg/mL. The cells were then passed twice through a French Pressure Cell at 18,000 psi. The cell debris was removed by centrifugation and the resulting supernatant was used as the cell free extract for enzyme assays.

PDC Enzyme Assay:

The reaction was initiated by the addition of 1.0 µL of enzyme to a 1.0 mL solution containing 25 mM phosphate buffer, pH 6.0, and 0.2 mM pHCA in a plastic, UV transparent cuvette. The reaction was then followed for 5 minutes spectrophotometrically at 315 nm at room temperature, using a molar extinction coefficient of 6000 $cm^{-1}$ for pHCA disappearance. The specific activity was expressed as micromoles of pHCA degraded per minute per milligram of protein.

Protein Assay:

The total protein concentration was determined with a protein assay kit (Bio-Rad Laboratories, Hecules, Calif.) with bovine serum albumin as the standard, according to the manufacturer's protocol.

Results:

The PDC specific activity of *B. subtilis, L. plantarum* and *P. fluorescens* increased upon induction with pHCA, as shown by the data in Table 3. In *L. plantarum*, the PDC activity increased from 0 to 1.7 U/mg of protein with addition of pHCA.

Bioconversion of pHCA to pHS by the Bacteria and Yeasts:

The bacteria *L. plantarum* and *B. subtilis*, and the yeasts, *Saccharomyces cerevisiae* and *Rhodotorula rubra* (ATCC#889), were grown in either LB medium or 2×YT medium, containing 1.0 mM pHCA, overnight at 30° C. After 18 h, samples of the culture media were taken for HPLC analysis, performed as described above. As can be seen from the results presented in Table 4, the bacterial strains tested exhibited 10 to 20-fold higher PDC activity than the yeast strains. Therefore, the pdc genes of *L. plantarum* and *B. subtilis* were chosen for cloning from the host strains for further metabolic engineering.

TABLE 4

Screening of Bacteria and Yeasts for the Ability to Convert pHCA to pHS

| Strain (ATCC #) | pHS Anaerobic Concentration (µM) | | | |
|---|---|---|---|---|
| | 1 h | 24 h | 48 h | 72 h |
| *Rhodotorula rubra* (889) | 0.0 | 0.0 | 2.5 | 10.4 |
| *Saccharomyces cerevisiae* (2034) | 0.0 | 9.4 | 24.4 | 39.5 |
| *Bacillus subtilis* (6633) | 427.9 | 430.5 | 488.0 | 456.6 |
| *Pseudomonas fluorescens* (11156) | 577.0 | 447.7 | 534.1 | 422.1 |
| *Pseudomonas putida* Type A (17453) | 0.0 | 0.0 | 0.0 | 0.0 |
| *Pseudomonas fluorescens* Type C (17559) | 0.0 | 0.0 | 0.0 | 0.0 |

Example 2

Characteristics of the PDC Enzme from *Lactobacillus plantarum* and *Bacillus subtilis*

The purpose of this Example was to overexpress the PDC enzyme from *Lactobacillus plantarum* and *Bacillus subtilis* in *E. coli* and to purify these enzymes for further characterization.

Cloning of the pdc Genes from *Lactobacillus plantarum* and *Bacillus subtilis*:

The pdc genes, SEQ ID NO:3 and SEQ ID NO:5, were amplified by PCR using genomic DNA from *L. plantarum* and *B. subtilis* as templates. The genomic DNA was isolated from *L. plantarum* grown on MRS medium and *B. subtilis* grown on LB medium using a DNeasy® Kit (Qiagen, Valencia, Calif.). The oligonucleotide primers used for the pdc1 gene, para-coumaric acid decarboxylase (GenBank Accession no. U63827), from *L. plantarum*, SEQ ID NO:3, were 5'-GGTAATT<u>CATATG</u>ACAAA-3' given as SEQ ID NO:9 and 5'-TCACGTGAAACATTACTTATT-3' given as SEQ ID NO:10, which included a NdeI site (underlined nucleotides). The oligonucleotide primers used for the *B. subtilis* pdc2, phenolic acid decarboxylase (GenBank Acces-

TABLE 3

Screening of PDC Activity in Cell-Free Extracts

| Strain | Protein Assay | | | PDC Activity | | | |
|---|---|---|---|---|---|---|---|
| | Induction by pHCA | OD 595 nm | µL | mg/mL | OD 315 nm/min | µL | U/mL | Specific Activity |
| *B. subtilis* | − | 0.9549 | 1 | 10.12 | 0.00779 | 10 | 0.13 | 0.0128 |
| *B subtilis* | + | 0.8154 | 1 | 7.2 | 0.01406 | 1 | 2.343 | 0.3257 |
| *L. plantarum* | − | 0.5580 | 10 | 0.24 | 0.0 | 50 | 0 | 0 |
| *L. plantarum* | + | 0.9534 | 5 | 2.02 | 0.02125 | 1 | 3.542 | 1.7561 |
| *P. fluorescens* | − | 0.8161 | 1 | 7.21 | 0.01414 | 1 | 0.236 | 0.0327 |
| *P. fluorescens* | + | 0.7779 | 1 | 6.41 | 0.03094 | 1 | 0.516 | 0.0804 | sion no. AF-17117) SEQ ID NO:5, were 5'-GTGTGT CATATGGAAAACT-3' given as SEQ ID NO:11 and 5'-TCGCGGGAATTGTGATGGT-3' given as SEQ ID NO:12, which also included a NdeI site (underlined nucleotides). The expected 550-bp DNA fragments for both pdc1 and pdc2 genes were purified using a Qiagen PCR Clean Up Kit and were ligated into the pCRII-TOPO cloning vector using the TA Cloning® Kit from Invitrogen. The transformations were done using One Shot® Chemically Competent *E. coli* (Invitrogen) according to the manufacturer's directions, except that 2×YT medium was used instead of SOC. The transformed cells were spread onto 50 μg/mL ampicillin plates containing X-gal and IPTG. From each of these plates, 10 white colonies were selected and restreaked onto ampicillin plates. The following procedures were done using cells transformed with pdc1 and cells transformed with pdc2 genes.

Each of the colonies was grown overnight on LB medium containing 50 μg/mL ampicillin. The plasmid was purified from the cells using the Qiagen Miniprep Kit. The plasmid was digested for 1 h at 37° C. with EcoRI to test for the presence of the insert. The digests were loaded on 1% agarose gels, along with kilobase markers, and electrophoresis was performed. Two bands were observed on the resulting gels, one at approximately 550 bp, corresponding to the insert, and one at 3.9 kbp, corresponding to the vector.

The cells containing the vector from one of the minipreps was grown overnight in a 50 mL culture containing 50 μg/mL ampicillin. The vector was purified from these cells using the Qiagen Midiprep QIAfilter according to the manufacturer's directions. The plasmid resulting from the *Lactobacillus plantarum* pdc gene was designated pDC1, while the plasmid resulting from the *Bacillus subtilis* pdc gene was designated pDC2. The inserts were sequenced at the DuPont Sequencing Facility using M13 forward and reverse primers in the vector to confirm the sequences. Computer analyses of the sequences were carried out by using Vector NTI (InforMax, Inc., Frederick, Md.) software.

The plasmid pDC1 was digested for 4 h at 37° C. using NdeI and EcoRI. The plasmid pDC2 was digested for 4 h at 37° C. using NdeI and NotI. The digests were loaded onto 1% agarose gels, along with kilobase markers, and electrophoresis was performed. A 555 bp band, corresponding to the insert, and a 3.9 kbp band, corresponding to the vector, were observed for the digest of pDC1. A 583 bp band, corresponding to the insert and a 3.9 kbp band, corresponding to the vector, were observed for the digest of pDC2. The insert bands were cut from the gel and purified using the Qiagen Gel Extraction Kit according to the manufacturer's protocol. The pET-17b vector, obtained from Novagen, Inc. (Madison, Wis.) was digested as described above and run on a 1% agarose gel. The vector band at 3.3 kbp, corresponding to the cut vector, was cut from the gel and purified using the Qiagen Gel Extraction Kit according to the manufacturer's protocol.

The pDC1 insert and the cut vector were ligated using T4 DNA ligase. Similarly, the pDC2 and the cut vector were ligated. The reactions were incubated for 1 h at room temperature. An aliquot from each reaction was used to transform B834(DE3)pLysS competent cells, which were obtained from Novagen, Inc., according to the manufacturer's directions. SOC medium was added to the transformed cells, and they were grown for 1 h at 37° C. Aliquots of these cultures were plated onto LB plates containing 50 μg/mL ampicillin and were grown overnight at 37° C. The colonies from these plates were restreaked onto fresh plates and then grown overnight in LB medium containing 100 μg/mL ampicillin. In the case of the pDC1 containing cells, the plasmid was isolated using the Qiagen Miniprep Kit and then digested using NdeI and NotI for 2 h. The digests were run on a 1% agarose gel, along with kilobase markers. All the clones except one were found to contain the insert. One of the clones that contained the insert was selected for expression studies. In the case of the pDC2 containing cells, samples of the cultures grown in LB medium containing 100 μg/mL ampicillin were boiled for approximately 10 min and then centrifuged for 5 min. Aliquots of these samples were transferred to PCR tubes and PCR was conducted as described above. Aliquots of the PCR reaction mixtures were run on a 1% agarose gel, along with kilobase markers. One of the clones was found to contain the insert. This clone was used for the expression studies.

The selected clones were grown in LB medium containing 100 μg/mL ampicillin. In the case of the pDC2 containing clone, the medium also contained 34 μg/mL chloramphenicol. These cultures served as the starter cultures. These starter cultures were used to inoculate fresh medium and the cells were grown at 37° C. to an OD of 0.5 to 1.0 measured at 600 nm. IPTG was then added to one of the pDC1 and one of the pDC2 containing cell cultures to a final concentration of 1 mM. The cultures were allowed to grow for 4 h at 37° C. Then, the cells were harvested by centrifugation and were frozen at −80° C. For further studies, the cells were thawed and then resuspended in 1 mL of 25 mM phosphate buffer (pH 6.0), containing leupeptin, pepstatin A, and E-64 each at 1 μg/mL, 40 μg/mL bestatin, 1 mM EDTA, 0.1 mg/mL AEBSF, and a small amount of DNase. The cells spontaneously lysed due to the presence of pLys and the resulting suspension was centrifuged for 10 min. The protein concentration and the PDC activity of the cell extracts were measured as described in Example 1. For both cells transformed with pDC1 and pDC2, the induced cells produced more protein of the expected molecular weight and the enzyme had a higher specific activity than that produced without induction. These results demonstrate the successful cloning and expression of the pdc genes from *Lactobacillus plantarum* and *Bacillus subtilis* in *E. coli*.

Recombinant Protein Purification from *E. coli*:

A single colony of each of the pDC1 and pDC2 transformed *E. coli* cells described above was picked and used to inoculate 10 mL of LB medium containing 100 μg/mL ampicillin. The cells were grown at 37° C. overnight on a shaker at 250 rpm. The next day, this culture was used to inoculate LB medium containing 100 μg/mL ampicillin. This culture was incubated at 37° C. for 4 h on a shaker at 250 rpm. When the cultures reached an OD of 0.6 at 600 nm, 1 mM IPTG was added. The cultures were incubated at 37° C. for 4 h on a shaker at 250 rpm and then the cells were harvested by centrifugation at 16,000×g for 20 min. The cells were resuspended in LB medium and centrifuged again at 9,000×g. The cells were resuspended in 25 mM phosphate buffer (pH 6.0) and passed twice through a French Press at maximum pressure. Cell debris was removed by centrifugation at 14,000 rpm for 30 min. The resulting supernatant was used as the cell free extract.

The cell free extract was fractionated by the addition of ammonium sulfate, as describe below. The 50% fraction containing the highest specific activity was used for purification by anion exchange chromatograph using an HQ column followed by hydrophobic interaction chromatography using a PE column, as described below.

Ammonium Sulfate Precipitation:

Saturated $(NH_4)_2SO_4$ was added to about 2.0 mL of cell free extract, to 30, 40 and 50% final concentration in the course of 15 min The sample was stirred on ice for another 15 min and then centrifuged in a bench top centrifuge for 15 min at maximum speed (14,000 rpm) at 4° C. The supernatant was saved for the next extraction step. The pellet was resuspended in 200 μL of 25 mM phosphate buffer, pH 6.0. All fractions were tested for PDC activity. The fraction with the highest specific activity (50% supernatant) was dialyzed against 1.0 L of 25 mM phosphate buffer for 2 h.

Anion Exchange Chromatography with HQ Column:

A 1.6 mL Poros® perfusion column (Roche Applied Science, Indianapolis, Ind.) was equilibrated in 25 mM phosphate buffer, pH 6.0 for 5× column volumes and then 1.0 mL of the dialyzed 50% supernatant was applied. After washing with phosphate buffer, the column was eluted in a KCl salt gradient, from 0.0 to 500 mM KCl in 20× column volumes. Fractions (0.8 mL) were collected and the fractions containing PDC activity were pooled and taken to the next step.

Hydrophobic Interaction Chromatography with PE Column:

Two milliliters of the pooled fractions from the anion exchange chromatography step was brought to 50% $(NH_4)_2SO_4$ saturation by adding 2.0 mL of 100% saturated ammonium sulfate. The pH was adjusted to 6.8 by adding 20 μL of 1.0 M NaOH. The resulting mixture was applied to a 1.6 mL Poros® PE column, which was equilibrated in 50% ammonium sulfate in 25 mM phosphate, pH 6.8. The PDC was eluted in a step gradient (50%–30%–20%) and the major activity eluted between 50% and 30%. Fractions containing high activity were pooled and tested. SDS-PAGE was used for each step of the purification.

PAGE Analysis:

The protein extracts containing PDC activity were resolved by denaturing SDS-polyacrylamide gel electrophoresis (PAGE) (12.5% resolving gel) with low molecular markers (14.4 to 9.4 kDa, Amersham Pharmacia Biotech, Piscataway, N.J.).

Characterization of the PDC Enzymes from *L. plantarum* and *B. subtilis*:

The characteristics of the PDC enzymes isolated from *L. plantarum* and *B. subtilis* were obtained using standard spectrometric and electrophoretic techniques and are listed in Table 5.

TABLE 5

Characteristics of the PDC enzyme from *L. plantarum* and *B. subtills*

|  | *L. plantarum* | *B. subtilis* |
| --- | --- | --- |
| MW (subunit) in kDa | 93 (23.5) | 45 (22) |
| Structure | Tetramer | Dimer |
| Cofactor Required | None | None |
| pH Optimum | 5.5–6.0 | 5.0 |
| Temperature Optimum | 30° C. | 40–45° C. |
| Isoelectric point (pI) | 4.9 | 5.0 |
| $K_M$ (mM) | 1.4 | 1.3 |

Example 3

Functional Expression of pdc Genes in *E. coli*

The phenylalanine overproducing strain *E. coli* NST74, available as strain ATCC No. 31884 from the American Type Culture Collection (ATCC), Manassas, Va., was tested for the ability to produce para-hydroxystyrene (pHS) when transformed with the pdc genes from *L. plantarum* (pdc1) or *B. subtilis* (pdc2). pHS can be produced from para-hydroxycinnamic acid (pHCA) by a one-step enzymatic reaction catalyzed by para-hydoxycinnamic acid decarboxylase (PDC). The two pdc genes, pdc1 from *L. plantarum*, SEQ ID NO:5, and pdc2 from *B. subtilis*, SEQ ID NO:7, were functionally expressed in *E. coli* NST74. The transformations were performed by electroporation as described below.

Cloning of pdc Genes from *Lactobacillus plantarum* and *Bacillus subtilis*:

The pdc genes, SEQ ID NO:3 and SEQ ID NO:5, were amplified by PCR using genomic DNA from *L. plantarum* and *B. subtilis* as templates. The genomic DNA was isolated from *L. plantarum* grown on MRS medium and *B. subtilis* grown on LB medium using a DNeasy® Kit (Qiagen, Valencia, Calif.). The oligonucleotide primers used for the pdc1 gene, para-coumaric acid decarboxylase (GenBank Accession no. U63827), from *L. plantarum*, SEQ ID NO:3, were 5'-GGTAATTCATATGACAAA-3', given as SEQ ID NO:9 and 5'-TCACGTGAAACATTACTTATT-3', given as SEQ ID NO:10, which included a NdeI site (underlined nucleotides). The oligonucleotide primers used for the *B. subtilis* pdc2, phenolic acid decarboxylase (GenBank Accession no. AF-17117) SEQ ID NO:5, were 5'-GTGTGT CATATGGAAAACT-3', given as SEQ ID NO:11 and 5'-TCGCGGGAATTGTGATGGT-3', given as SEQ ID NO:12, which also included a NdeI site (underlined nucleotides). The expected 550-bp DNA fragment for both pdc1 and pdc2 genes were purified using a Qiagen PCR Clean Up Kit and were ligated into the pCRII-TOPO cloning vector using the TA Cloning® Kit from Invitrogen. Subsequently, these plasmids were digested with BamHI and XbaI and the fragments containing the pdc genes were ligated into pKSM715 (obtained from ATCC), which had been previously digested with BamHI and XbaI, to form pKSM-pdc1 and pKSM-pdc2, respectively.

Preparation of Electro-Competent *E. coli* Cells:

Samples of glycerol stocks of the phenylalanine overproducing *E. coli* strain NST74 were spread onto agarose plates without any antibiotics and incubated overnight at 37° C. A single colony was picked, inoculated into 4.0 mL of LB medium and grown overnight at 37° C. One liter of LB medium was inoculated with a 1/100 volume of the fresh overnight culture. The cells were grown at 37° C., with vigorous shaking, to an OD of approximately 0.5 to 0.7 at 600 nm. The cells were centrifuged in cold centrifuge bottles in a cold rotor at 4000×g for 15 min. The supernatants were discarded and the cell pellets were gently resuspended in a total of 1.0 L of ice-cold 10% glycerol. The cells were centrifuged as described above and then resuspended in 0.5 L of ice-cold 10% glycerol. The above procedures were repeated to obtain the cells, which were resuspended in 250 mL of ice-cold 10% glycerol and washed again. The cell pellets obtained from the last washing were resuspended into a final volume of 3.0–4.0 mL in ice-cold 10% glycerol. The cell suspension was frozen in aliquots on dry ice, and stored at −80° C.

Transformation and Selection Procedures:

The electro-competent *E. coli* cells, described above, were thawed on ice and plasmid DNA (~50 ng, of the plasmids pKSM-pdc1 or pKSM-pdc2, described above) was added to the tubes containing the cells. The DNA/cell suspensions were then transferred to pre-chilled electroporation cuvettes (0.1 cm, Bio-Rad, Hercules, Calif.) and the cuvettes were kept on ice. Each sample was electrically pulsed at 18 kV/cm in a Gene Pulser (Bio-Rad) (25 µF, 200 ohm). SOC medium (1.0 mL) was added to each cuvette immediately after pulsing. The cell mixtures were then transferred to tubes and left on the shaker (1.0 h at 37° C., and shaken at 220 rpm). Samples (100 µL) of each transformation reaction were then pipetted onto separate LB plates and incubated overnight at 37° C. The LB plates contained either 100 µg/mL ampicillin or 50 µg/mL kanamycin.

Para-Hydroxystyrene Biosynthesis by Recombinant *E. coli*:

For bioconversion of pHCA to pHS, the cells of recombinant *E.coli* strains containing the pdc1 or pdc2 gene were first streaked out from glycerol stocks onto the LB agar plates containing the appropriate antibiotic. Single colonies were selected and grown in LB medium containing the antibiotic overnight as the seed culture. The seed culture was then inoculated into LB medium (OD at 600 nm of approximately 0.5). The cultures were induced with 1.0 mM IPTG in the presence of 1.0 mM pHCA. When the induced cells were left for 60 h with 1.0 mM pHCA, the pHS formed was detectable using the HPLC method described above. As shown by the data in Table 6, the pdc1 transformant generated 0.60 mM pHS, a slightly higher amount of pHS than that produced by the pdc2 transformant (0.52 mM). The data in Table 6 is expressed as the average of one representative experiment performed in triplicate. These in vivo results indicate that the PDC enzyme from *L. plantarum* (pdc1) had a slightly higher activity with pHCA as substrate than the enzyme from *Bacillus subtilis* (pdc2).

TABLE 6

Conversion of pHCA to pHS by *E. coli* NST74 Expressing pdc1 or pdc2

| Isolate | pHCA (mM) | pHS (mM) |
|---|---|---|
| Control | 0.860 | 0 |
| pdc1 | 0.061 | 0.60 |
| pdc2 | 0.081 | 0.52 |

Example 4

Co-expression of pdc1 and pal in the Phenylalanine Overproducing *E. coli* Strain The pdc1 gene was co-transformed with the pal gene from *R. glutinis* (SEQ ID NO:1) into *E. coli* NST74.

Cloning of the pal Gene from *Rhodotorula glutinis*:

The *Rhodotorula glutinis* (ATCC No. 10788) pal gene, SEQ ID NO:1 (GenBank Accession no. M18261), was amplified from reverse-transcribed RNA that was purified from exponential phase cells grown in the complex medium containing phenylalanine. The gene sequence of pal from various sources, including *Rhodosporidium toruloides* also known as *Rhodotorula glutinis*, has been determined and published (Edwards et al., *Proc. Natl. Acad. Sci., USA* 82:6731–6735 (1985); Cramer et al., *Plant Mol. Biol.* 12:367–383 (1989); Lois et al., *EMBO J.* 8:1641–1648 (1989); Minami et al., *Eur. J. Biochem.* 185:19–25 (1989); Anson et al., *Gene* 58:189–199 (1987); Rasmussen & Oerum, *DNA Sequence*, 1:207–211 (1991)).

The *Rhodotorula glutinis* mRNA was reversed transcribed according to the Perkin Elmer (Norwich, Conn.) GeneAmp Kit instructions without diethylpyrocarbonate (DEPC) treated water. The primers used were the random hexamers supplied with the kit. Primers used to amplify the pal gene included the upstream primer 5'-ATAGTAGAAT-TCATGGCACCCTCGCTCGACTCGA-3' (SEQ ID NO:7) containing an EcoRI restriction site, and a downstream PCR primer 5'-GAGAGACTGCAGAGAGGCAGCCAA-GAACG-3' (SEQ ID NO:8) containing a PstI restriction site which were synthesized based on the *Rhodosporidium toruloides* pal gene. PCR fragments were digested with EcoRI and PstI and ligated to pKK223-3 previously cut with EcoRI and PstI forming pCA16.

Co-expression of pdc1 and pal in *E. coli* NST74:

*E. coli* NST74 cells were transformed according to the procedure described in Example 3 using pCA16 for pal expression and pKSM-pdc1 for pdc1 or pKSM-pdc2 for pdc2 expression.

These transformed cells containing both pal and pdc genes were selected with both 100 µg/mL of ampicillin and 50 µg/mL of kanamycin and cultured as described above without pHCA addition in the minimal medium. Samples of the cultures were taken at 2, 4, 6, 8, 24, 48, and 60 h after IPTG induction and analyzed by HPLC as described above. These pal/pdc transformants produced pHCA, cinnamate and pHS when grown in either LB or M9 medium with glucose for 60 h, as shown by the results in Table 7.

TABLE 7

Production of pHCA, CA, and pHS by pal/pdc Transformants

| Isolate | pHCA (mM) | CA (mM) | pHS (mM) |
|---|---|---|---|
| Control | 0 | 0 | 0 |
| pal/pdc2 | 0.03 | 0.52 | 0.11 |
| pal/pdc2 | 0.61 | 0.91 | 0.01 |

For pHS production, the transformants were selected on an LB agar plate with the appropriate antibiotics and grown in either LB or M9 medium for 60 h. Concentrations of phenylalanine and tyrosine in these cultures were measured using the HPLC method described above and the results are depicted in Table 8. While the level of phenylalanine in cultures of both pal/pdc1 and pal/pdc2 transformants is similar to that of the control, the concentration of tyrosine in the pal/pdc1 cultures is far less than that in the pal/pdc2 cultures. Lower tyrosine in the pal/pdc1 transformant culture indicates higher specific activity of the PDC1 enzyme.

TABLE 8

Concentrations of Phenylalanine and Tyrosine in Cultures of pal/pdc Transformants

| Isolate | Phenylalanine (mM) | Tyrosine (mM) |
|---|---|---|
| Control | 1.225 | 0.759 |
| pal/pdc2 | 1.107 | 0.374 |
| pal/pdc2 | 1.068 | 0.602 |

Example 5

Optimization of pHS Production by pal/pdc1 Transformants

Since pal/pdc1 transformants showed higher activity for pHS production, they were chosen for further studies. These transformants were grown in M9 medium with glucose and the levels of pHCA, pHS, and CA were determined after 6 and 60 h following induction with IPTG using the HPLC method described above. As can be seen from the results presented in Table 9, only small amounts of pHCA were observed at 6 h, while no pHCA was observed at 60 h. The concentration of cinnamate (CA) increased from around 0.1 mM to around 0.25 mM after 60 h, attesting to the fact that most of the cinnamate formed was remaining in the cultures. No pHCA was observed in the 60 h cultures, but the concentration of pHS had increased from around 0.05 mM in the 6 h sample to around 0.30 mM after 60 h.

TABLE 9

Production of pHCA, CA, and pHS by the pal/pdc1 Transformant

| Isolate | pHCA (μM) | CA (μM) | pHS (μM) |
| --- | --- | --- | --- |
| Control | 0 | 0 | 0 |
| pal/pdc1 induced for 6 h | 5.63 | 99.12 | 54.27 |
| pal/pdc1 induced for 60 h | 0.57 | 221.33 | 297.03 |

The levels of phenylalanine and tyrosine were measured in the above cultures after 6 and 60 h using HPLC and levels measured after 6 h are given in Table 10. The control cultures contained around 0.3 mM phenylalanine and 0.03 mM tyrosine after 6.0 h of growth. While analysis of the pal/pdc1 transformant cultures did not indicate the presence of any phenylalanine, very small amounts of tyrosine were observed. Analysis of the 60 h samples indicated the presence of around 0.3 mM phenylalanine in the pal/pdc1 transformant cultures while no tyrosine was detectable (Table 11).

TABLE 10

Consumption of Phenylalanine and Tyrosine by the pal/pdc1 Transformant Grown in M9 Medium After 6 h

| Isolate | Phenylalanine (μM) | Tyrosine (μM) |
| --- | --- | --- |
| Control | 309.71 | 26.11 |
| pal/pdc1 | 0 | 11.51 |

TABLE 11

Consumption of Phenylalanine and Tyrosine by the pal/pdc1 Transformant Grown on M9 medium with Glucose After 60 h

| Isolate | Phenylalanine (μM) | Tyrosine (μM) |
| --- | --- | --- |
| Control | 590.24 | 46.34 |
| pal/pdc1 | 284.14 | 0 |

The experiments outlined above constitute the first example of successful co-expression of pal from yeast and pdc genes from *Lactobacillus* and *Bacillus* species in a phenylalanine over-producing *E. coli* strain for conversion of glucose to pHS. Our results also indicate that more detailed studies on the growth kinetics and the gene expression of the organisms developed are needed. Of particular significance is the toxic effect of the pHS formed in the cultures on various enzyme activities of the host organism.

Example 6

Growth Kinetic Studies with Recombinant *E. coli* NST74 Strains Containing Both pal and pdc Genes for Conversion of Glucose to pHS Two strains (designated as WWQ51.1 and WSQ1) were constructed from the *E. coli* phenylalanine overproducing strain *E. coli* NST74 by transformation with pCA16 and pKSM-pdc1 and selection for ampicillin and kanamycin resistance, as described in Example 4. Since preliminary experiments showed similar patterns for both constructs, we chose strain WWQ51.1 for further studies.

An *E. coli* strain containing the wild type pal/tal gene (PAL/TAL ratio of 2.0) uses both PAL and TAL routes to convert glucose to both CA and pHCA. In addition, our previous kinetic studies with the PAL/TAL enzyme had indicated that the enzyme had a higher Vmax for PAL (5.5) versus TAL (0.76). Based on the kinetic information it is expected that the presence of phenylalanine would interfere with the TAL activity of the enzyme. In addition, the low $K_i$ of pHCA on TAL activity (16 μM) underlines the possibility that slight accumulation of pHCA could inhibit the TAL activity.

Based on our previous findings, we offer the following explanations for our current observations with the *E. coli* strain containing both pal/tal and the pdc genes. In these double transformants, the pHCA formed is converted to pHS. The amount of pHS formed in this process is more than the amount of pHCA formed in the strain containing only the pal/tal gene. One explanation for this observation could be that removal of the pool of pHCA and its conversion to pHS removes the potential inhibition of the TAL activity (by high pHCA concentrations), facilitating further pHCA production which leads to pHS formation. It is also possible that removal of tyrosine by the TAL activity, could abolish the feedback inhibition of chorismate/p-prephenate dehydratase by tyrosine, allowing more optimal functioning of the system. Some residual concentrations of pHCA observed in cultures of strains containing both pal/tal and pdc genes underline the need for higher in vivo expression levels of the PDC activity for complete transformation of pHCA to pHS.

Example 7

Effects of pal/pdc1 Gene Expression on the Growth of the Phenylalanine Overproducing *E. coli* Transformants The phenylalanine overproducing strain *E. coli* NST74 transformed with both pCA16 and pKSM-pdc1 (see Example 4), which contain the wild type pal gene and the pdc1 gene from *L. plantarum*, were inoculated into LB medium with or without IPTG induction. Table 12 shows growth kinetic results of this study as indicated by cell density measured at an absorbance of 600 nm. Growth of the pal/pdc transformants of strain *E. coli* NST74 started to slow down upon addition of IPTG for about 3.0 h and was maintained at a lower rate for up to 7.0 h. The control used was the same strain grown without IPTG. The results indicated slower growth in the presence of IPTG, probably due to the formation of pHCA and pHS, which have been shown to be toxic to the cells. Previous studies had indicated that both pHCA and pHS are toxic to the cells with pHS showing toxicity at concentrations as low as 0.5 g/L.

TABLE 12

Growth Kinetics of pal/pdc1 Transformants

| Induction Time (h) | OD 600 nm Without IPTG | OD 600 nm With IPTG |
|---|---|---|
| 0 | 1.34 | 1.35 |
| 1 | 1.52 | 1.53 |
| 2 | 1.64 | 1.52 |
| 3 | 1.64 | 1.62 |
| 4 | 1.74 | 1.68 |
| 5 | 1.81 | 1.71 |
| 6 | 1.84 | 1.76 |
| 7 | 1.79 | 1.78 |

Phenylalanine was rapidly consumed in cultures induced with IPTG and disappeared after 6 h of induction, while it remained almost unchanged in uninduced cultures (Table 13).

TABLE 13

Phenylalanine Consumption by pal/pdc1 Transformants

| | Phenylalanine (mM) | |
|---|---|---|
| Induction Time (h) | Without IPTG | With IPTG |
| 0 | 0.77 | 0.76 |
| 1 | 0.78 | 0.82 |
| 2 | 0.83 | 0.73 |
| 3 | 0.72 | 0.61 |
| 4 | 0.68 | 0.38 |
| 5 | 0.67 | 0.47 |
| 6 | 0.62 | 0 |
| 7 | 0.63 | 0 |

Complete consumption of phenylalanine, within 6.0 h of induction by IPTG, was achieved by the pal/pdc1 transformant (Table 13). However, the recombinant strain without IPTG induction showed a slight consumption of phenylalanine. This observation could be explained by small levels of expression from the promoter of the pCA16 plasmid, derived from pKK223, carrying the wild type pal/tal gene and the presence of the pKSM715 (which is tightly controlled by IPTG) in the same cell. Following induction, cinnamic acid (CA) was also produced (Table 14) and accumulated in the medium.

TABLE 14

CA formation by pal/pdc1 Transformants

| | CA (mM) | |
|---|---|---|
| Induction Time (h) | Without IPTG | With IPTG |
| 0 | 0.026 | 0.027 |
| 1 | 0.043 | 0.063 |
| 2 | 0.032 | 0.322 |
| 3 | 0.081 | 0.421 |
| 4 | 0.062 | 0.811 |
| 5 | 0.072 | 0.667 |
| 6 | 0.145 | 0.678 |
| 7 | 0.202 | 0.844 |

Consumption of tyrosine by the pal/pdc1 transformants began after 2.0 h of induction with IPTG and continued for up to 7.0 h (Table 15). The control, which was not induced with IPTG, maintained a constant level of tyrosine in the medium during the course of the experiment (Table 15). Disappearance of tyrosine was concomitant with the appearance of pHCA (Table 16) and pHS (Table 17) in the medium. Without IPTG induction, no pHS and some pHCA could be observed. However, when induced with IPTG, the pHS concentration in the medium started to increase (Table 17). It was interesting to note that while pHS was being formed, the concentration of pHCA remained steady (Table 16). One explanation for this observation could be that removal of pHCA for conversion to pHS might stimulate pHCA production by removing its inhibition of the TAL enzyme. After 6.0 h of induction, pHS in the medium started to decline. The presence of pHCA in the culture medium at the completion of the experiment was indicative of the lack of sufficient PDC activity for its conversion to pHS.

TABLE 15

Consumption of Tyrosine by pal/pdc1 Transformants

| Induction | Tyrosine (mM) | |
|---|---|---|
| Time (h) | Without IPTG | With IPTG |
| 0 | 0.194 | 0.193 |
| 1 | 0.229 | 0.221 |
| 2 | 0.235 | 0.195 |
| 3 | 0.239 | 0.151 |
| 4 | 0.242 | 0.112 |
| 5 | 0.224 | 0.091 |
| 6 | 0.229 | 0.073 |
| 7 | 0.256 | 0.049 |

TABLE 16 pHCA Formation by pal/pdc1 Transformants

| Induction | pHCA (mM) | |
|---|---|---|
| Time (h) | Without IPTG | With IPTG |
| 0 | 0.011 | 0.012 |
| 1 | 0.016 | 0.012 |
| 2 | 0.021 | 0.042 |
| 3 | 0.029 | 0.053 |
| 4 | 0.027 | 0.097 |
| 5 | 0.031 | 0.167 |
| 6 | 0.054 | 0.185 |
| 7 | 0.071 | 0.163 |

TABLE 17 pHS Formation by pal/pdc1 Transformants

| | pHS (µM) | |
|---|---|---|
| Induction Time (h) | Without IPTG | With IPTG |
| 0 | 0 | 0 |
| 1 | 0 | 0 |
| 2 | 0 | 0.112 |
| 3 | 0 | 0.274 |
| 4 | 0 | 0.387 |
| 5 | 0 | 0.369 |
| 6 | 0 | 0.451 |
| 7 | 0 | 0.318 |

Example 8

Fermentation of Glucose to pHS in Flasks

*E. coli* strain WWQ51.1, described in Example 6, was grown in 250 mL baffled flasks in 50 mL of medium to test production of pHS from glucose. The medium contained 0.5 g/L MgSO$_4$, 4 g/L (NH$_4$)$_2$SO$_4$, 0.1 M MOPS, K$_2$HPO$_4$/KH$_2$PO$_4$ to 1 g/L PO$_4$, 1 mg/L thiamine, 15 g/L glucose, trace metals including citric acid (100 mg/L), CaCl$_2$ (15 mg/L), FeSO$_4$-7H$_2$O (25 mg/L), ZnSO$_4$-7H$_2$O (2 mg/L), CuSO$_4$-5H$_2$O (2 mg/L), COCl$_2$-6H$_2$O (12 mg/L), and MnCl$_2$-4H$_2$O (1.5 mg/L). The antibiotics, kanamycin (50 ppm) and ampicillin (100 ppm) were added. IPTG was added as an inducer at 0.5 mM. The pH was adjusted to 6.8–7.0 with concentrated KOH or HCl. Seed cultures were grown for 16 h and then diluted in fresh medium to an OD, of 0.1 to 0.2, measured at 550 nm (OD$_{550}$), in duplicate flasks. These cultures were allowed to incubate at 300 rpm and 35° C. for 50 h and samples were taken at 0, 9, 25, and 50 h for analysis by HPLC. The results are presented in Table 18. Fifty hours of fermentation produced 64–68 mg/L of pHS with a yield of 0.0051–0.0052 g pHS/g glucose utilized.

TABLE 18

Fermentation of Glucose to pHS by *E. coli* WWQ51.1 in Flasks

| Time/Run | OD 550 nm | pH | pHS (mg/L) | Glucose (g/L) | Phenylalanine (g/L) | Tyrosine (g/L) | pHCA (g/L) | CA (g/L) | pHS yield (g/g) |
|---|---|---|---|---|---|---|---|---|---|
| 0 h | | | | | | | | | |
| Run 1 | 0.123 | | 0.04 | 17.5 | 0.01 | 0.00 | 0.00 | 0.00 | |
| Run 2 | 0.123 | | 0.04 | 17.7 | 0.01 | 0.00 | 0.00 | 0.00 | |
| 9 h | | | | | | | | | |
| Run 1 | 6.8 | | 16 | 11.4 | 0.09 | 0.00 | 0.00 | 0.14 | |
| Run 2 | 7.2 | | 11 | 12.4 | 0.09 | 0.00 | 0.00 | 0.14 | |
| 25 h | | | | | | | | | |
| Run 1 | 10.2 | 4.55 | 65 | 4.73 | 0.44 | 0.12 | 0.00 | 0.33 | |
| Run 2 | 9.9 | 4.55 | 42 | 4.53 | 0.46 | 0.13 | 0.00 | 0.36 | |
| 50 h | | | | | | | | | |
| Run 1 | | | 64 | 4.97 | 0.44 | 0.12 | 0.00 | 0.32 | 0.0051 |
| Run 2 | | | 68 | 4.57 | 0.46 | 0.13 | 0.00 | 0.36 | 0.0052 |

Example 9

Fermentation of Lactose to pHS

As an alternative carbon source, lactose was tested as a fermentation substrate for production of pHS by *E. coli* strain WWQ51.1. Seed flasks were incubated for 12 h and cells from these flasks were inoculated to fresh medium in the test flasks. The seed medium for this fermentation was identical to that used in Example 8, except that lactose was substituted for glucose. Test flasks were 250 mL baffled flasks and contained 50 mL culture medium with 15.5 g/L lactose at the time of inoculation. These were incubated at 35° C. at 300 rpm for 4 days. IPTG was added to these flasks at either 0 mM, 0.5 mM, or 5 mM concentration to induce gene expression from the plasmids. Fermentation of lactose to pHS, as indicated in Table 19, was significantly better than fermentation of glucose to pHS. The best results were obtained with 5 mM IPTG, reaching a titer of 0.249 g/L and a yield of 0.021–0.024 g pHS per g lactose utilized.

TABLE 19

Lactose Fermentation to pHS by *E. coli* WWQ51.1

| Flask # | IPTG (mM) | pHS (g/L) | Tyrosine (g/L) | Phenylalanine (g/L) | pHCA (g/L) | CA (g/L) | Lactose (g/L) | pH | OD$_{550}$ | pHS yield g pHS/g lactose |
|---|---|---|---|---|---|---|---|---|---|---|
| 1 | 0 | 0.17 | 0.43 | 0.68 | 0.03 | 0.82 | 1.75 | 6.16 | 10.7 | 0.012 |
| 2 | 0 | 0.182 | 0.42 | 0.69 | 0.03 | 0.84 | 1.72 | 6.22 | 11.4 | 0.013 |
| 3 | 0.5 | 0.192 | 0.37 | 0.60 | 0.04 | 0.95 | 1.77 | 6.21 | 11.8 | 0.014 |

TABLE 19-continued

Lactose Fermentation to pHS by *E. coli* WWQ51.1

| Flask # | IPTG (mM) | pHS (g/L) | Tyrosine (g/L) | Phenyl-alanine (g/L) | pHCA (g/L) | CA (g/L) | Lactose (g/L) | pH | OD$_{550}$ | pHS yield g pHS/g lactose |
|---|---|---|---|---|---|---|---|---|---|---|
| 4 | 0.5 | 0.189 | 0.34 | 0.56 | 0.03 | 0.87 | 1.88 | 6.21 | 12.2 | 0.014 |
| 5 | 5 | 0.249 | 0.12 | 0.08 | 0.01 | 0.74 | 3.82 | 6.38 | 10.4 | 0.021 |
| 6 | 5 | 0.127 | 0.11 | 0.11 | 0.01 | 0.88 | 4 | 6.42 | 11 | 0.024 |

Example 10

Fermentation of Glucose to pHS at 10 L Scale

The production of pHS from glucose in a 14 L Braun Biostat C fermentor (B. Braun Biotech International Gmbh, Melsungen, Germany) was tested under phosphate (PO$_4$) limiting conditions. *E. coli* strain WWQ51.1 was grown in a seed culture for 12 h prior to inoculation of the fermentor. IPTG (0.5 mM) was added to the fermentor at 6.72 h.

Fermentation Protocol:

The vessel medium was prepared in an initial batch of 7 L containing 1.6 g KH$_2$PO$_4$, 15.0 g MgSO$_4$, 8.0 mL Mazu DF204 antifoam (BASF Corporation, Mount Olive, N.J.), and 8 mg thiamine. Following sterilization, 240 g glucose solution (50% w/w), 160 mL trace element solution (Table 20) and 50 mg/L kanamycin and 100 mg/L ampicillin were added to a final volume of 8 L. Ammonium hydroxide (40% w/v) and 20% w/v H$_2$SO$_4$ were used for pH control. The set points for agitation, aeration, pH, pressure and dissolved oxygen (DO) are described in Table 21 below. The dissolved oxygen concentration (DO) was controlled at 25% of air saturation initially with agitation to rise with increased oxygen demand, followed by aeration. The 500 mL seed culture was grown in a 2 L flask at 35° C., at 300 rpm for 12 h to an OD$_{550}$ of approximately 2.0. IPTG was added to 0.5 mM after the OD$_{550}$ reached 4 in the fermentor. The glucose feed was started at 1–5 g/L and the following formula was used to adjust the glucose feed for cell growth:

feed rate (g/min)=OD$_{550}$×fermentation volume (L)× 0.0022.

The glucose feed rate was reduced if glucose accumulated above 2 g/L.

TABLE 20

Trace Elements Solution

| Chemical | Concentration (g/L) |
|---|---|
| Citric acid | 10 |
| CaCl$_2$—2H$_2$O | 1.5 |
| FeSO$_4$—7H$_2$O | 5 |
| ZnSO$_4$—7H$_2$O | 0.39 |
| CuSO$_4$—5H$_2$O | 0.38 |
| CoCl$_2$—6H$_2$O | 0.2 |
| MnCl$_2$—4H$_2$O | 0.3 |

TABLE 21

Fermentation Run Conditions

| | Initial Set-Point | Minimum | Maximum |
|---|---|---|---|
| Stirrer (rpm) | 400 | 400 | 1000 |
| Airflow (slpm) | 2 | 2 | 2 |
| pH | 6.5 | 6.5 | 6.5 |
| Pressure (psig) | 0.5 | 0.5 | 0.5 |
| DO | 25% | 25% | 25% |

The kinetics of glucose fermentation to pHS are presented in Table 22. pHS production reached 0.40 g/L after about 56 h of fermentation.

TABLE 22

Fermentation of Glucose to pHS at 14 L Scale

| Time (h) | OD$_{550}$ | pHS (g/L) | pHCA (g/L) | CA (g/L) | Phenyl-alanine (g/L) | Tyrosine (g/g) |
|---|---|---|---|---|---|---|
| 4.6 | 5.4 | 0.00 | 0.00 | 0.03 | 0.10 | 0.00 |
| 6.4 | 8.9 | 0.01 | 0.01 | 0.05 | 0.20 | 0.00 |
| 8.1 | 18.4 | 0.01 | 0.01 | 0.11 | 0.39 | 0.00 |
| 11.1 | 23.2 | 0.04 | 0.03 | 0.35 | 0.54 | 0.00 |
| 13.1 | 25.0 | 0.05 | 0.03 | 0.42 | 0.51 | 0.00 |
| 15.8 | 25.2 | 0.08 | 0.02 | 0.51 | 0.52 | 0.00 |
| 17.9 | 25.0 | 0.11 | 0.02 | 0.59 | 0.49 | 0.00 |
| 19.8 | 25.4 | 0.11 | 0.02 | 0.64 | 0.43 | 0.00 |
| 23.0 | 32.2 | 0.14 | 0.02 | 0.72 | 0.46 | 0.00 |
| 26.0 | 27.0 | 0.18 | 0.02 | 0.84 | 0.43 | 0.00 |
| 29.0 | 27.6 | 0.19 | 0.02 | 0.91 | 0.47 | 0.00 |
| 32.1 | 30.0 | 0.22 | 0.02 | 0.94 | 0.43 | 0.00 |
| 34.9 | 27.4 | 0.21 | 0.02 | 0.99 | 0.47 | 0.00 |
| 38.1 | 27.6 | 0.26 | 0.01 | 1.07 | 0.52 | 0.00 |
| 40.2 | 20.4 | 0.28 | 0.01 | 1.08 | 0.51 | 0.00 |
| 41.8 | 22.0 | 0.29 | 0.01 | 1.09 | 0.50 | 0.00 |
| 44.4 | 34.2 | 0.27 | 0.01 | 1.11 | 0.50 | 0.00 |
| 47.0 | 25.6 | 0.30 | 0.01 | 1.12 | 0.48 | 0.00 |
| 50.1 | 26.2 | 0.33 | 0.01 | 1.17 | 0.48 | 0.00 |
| 53.0 | 22.6 | 0.38 | 0.01 | 1.19 | 0.47 | 0.00 |
| 56.3 | 28.0 | 0.40 | 0.01 | 1.15 | 0.41 | 0.00 |

What is claimed is:

1. A method for the production of para-hydroxystyrene comprising:
   (i) contacting a recombinant host cell with a fermentable carbon substrate, said recombinant host comprising:
   a) at least one gene encoding a polypeptide having tyrosine ammonia lyase activity comprising the amino acid sequence as set forth in SEQ ID NO:2; and
   b) at least one gene encoding a polypeptide having para-hydroxycinnamic acid decarboxylase activity comprising an amino acid sequence as set forth in SEQ ID NO:4 or 6;
   (ii) growing said recombinant cell for a time sufficient to produce para-hydroxystyrene; and
   (iii) optionally recovering said para-hydroxystyrene.

2. A method according to claim 1 wherein said fermentable carbon substrate is selected from the group consisting of monosaccharides, oligosaccharides, polysaccharides, carbon dioxide, methanol, formaldehyde, formate, and carbon-containing amines.

3. A method according to claim 2 wherein said fermentable carbon substrate is selected from the group consisting of glucose and lactose.

4. A method according to claim 1 wherein said recombinant host cell is selected from the group consisting of bacteria, yeast, filamentous fungi, cyanobacteria algae and plant cells.

5. A method according to claim 4 wherein said recombinant host cell is selected from the group consisting of *Escherichia, Salmonella, Bacillus, Acinetobacter, Streptomyces, Corynebacterium, Methylosinus, Methylomonas, Rhodococcus, Pseudomonas, Rhodobacter, Synechocystis; Saccharomyces, Zygosaccharomyces, Kluyveromyces, Candida, Hansenula, Debaryomyces, Mucor, Pichia, Torulopsis, Aspergillus, Arthrobotrys, Brevibacteria, Microbacterium, Arthrobacter,* and *Citrobacter.*

6. A method according to claim 4 wherein said recombinant host cell is a tyrosine overproducing strain.

7. A method according to claim 1 wherein said recombinant host cell is a cell isolated from plants selected from the group consisting of soybean, rapeseed, sunflower, cotton, corn, tobacco, alfalfa, wheat, barley, oats, sorghum, rice, broccoli, cauliflower, cabbage, parsnips, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

8. A method according to claim 1 wherein said gene encoding a polypeptide having tyrosine ammonia lyase activity encodes the polypeptide having a catalytic efficiency for tyrosine of about $4.14 \times 10^3$ $M^{-1}sec^{-1}$ to about $1 \times 10^9$ $M^{-1}sec^{-1}$.

9. A method according to claim 1 wherein the gene encoding a polypeptide having tyrosine ammonia lyase activity is derived from *Rhodotorula glutinis.*

10. A method according to claim 1 wherein the gene encoding a polypeptide having para-hydroxycinnamic acid decarboxylase activity is derived from *Lactobacillus plantarum.*

* * * * *

SEQUENCE LISTING

<160> NUMBER OF SEQ ID NOS: 18

<210> SEQ ID NO 1
<211> LENGTH: 2703
<212> TYPE: DNA
<213> ORGANISM: Rhodotorula glutinis

<400> SEQUENCE: 1

```
atggcaccct cgctcgactc gatctcgcac tcgttcgcaa acggcgtcgc atccgcaaag      60
caggctgtca atggcgcctc gaccaacctc gcagtcgcag gctcgcacct gccccacaac     120
ccaggtcacg caggtcgaca tcgtcgagaa gatgctcgcc gcgccgaccg actcgacgct     180
cgaactcgac ggctactcgc tcaacctcgg agacgtcgtc tcggccgcga ggaagggcag     240
gcctgtccgc gtcaaggaca gcgacgagat ccgctcaaag attgacaaat cggtcgagtt     300
cttgcgctcg cagtgagagt cgtgctttcg ttctctggcg tcgagagggc gggaccttcc     360
caagttgcca agggactgac tgtcgctctc ctgtgtcgcg cagactctcc atgagcgtct     420
acggcgtcac gactggattt gcggatccgc agacacccg caccgaggac gccatctcgc     480
tccagaaggc gtgcgtcctc ctcgtctccc tctcgcttct cgagcttcgg actgaccgtc     540
ttcccgcaca gtcctcgta gcaccagctc tgcggtgttc tcccttcgtc gttcgactcg     600
ttccgcctcg gccgcggtct cgagaactcg cttcccctcg aggttgttcg cggcgccatg     660
acaatccgcg tcaacagctt gacccggtga gttgccgtcc ttactcactc agcggtcttc     720
gagctgacag ttggcgcacc cagcggccac tcggctgtcc gcctcgtcgt cctcgaggcg     780
ctcaccaact tcctcaacca cggcatcacc cccatcgtcc cctccgcgg caccatctct     840
gcgtcgggcg acctctctcc tctctcctac attgcagcgg ccatcagcgg tcacccggac     900
agcaaggtgc acgtcgtcca cgagggcaag gagaagatcc tgtacgcccg cgaggcgatg     960
gcgctcttca acctcgagcc cgtcgtcctc ggcccgaagg aaggtctcgg tctcgtcaac    1020
ggcaccgccg tctcagcatc gatgccacc ctcgctctgc acgacgcaca catgctctcg    1080
ctcctctcgc agtcgctcac ggccatgacg gtcgaagcga tggtcggcca cgccggctcg    1140
ttccacccct tccttcacga cgtcacgcgc cctcacccga cgcagatcga agtcgcggga    1200
aacatccgca agctcctcga gggaagccgc tttgctgtcc accatgagga ggaggtcaag    1260
gtcaaggacg acgagggcat tctccgccag gaccgctacc ccttgcgcac gtctcctcag    1320
gtgcgcttac ttctgtttgt tctgccgaag acatgacgct gacgtccgct tactcgcgca    1380
gtggctcggc ccgctcgtca gcgacctcat tcacgcccac gccgtcctca ccatcgaggc    1440
cggccagtcg acgaccgaca accctctcat cgacgtcgaa acaagactt cgcaccacgg    1500
cggcaatttc caggctgccg ctgtggccaa caccatggag aagactcggt gcgccgcttc    1560
actgtgacct gttctcttgg tctcgtcctg acgagtacgc tgtgcagcct cgggctcgcc    1620
cagatcggca agctcaactt cacgcagctc accgagatgc tcaacgccgg catgaaccgc    1680
ggcctccccc cctgcctcgc ggccgaagac ccctcgctct cctaccactg caagggcctc    1740
gacatcgccg ctgcggcgta cacctcggag ttgggacacc tcgccaaccc tgtgacgacg    1800
catgtccagc cggctgagat ggcgaaccag gcggtcaact cgcttgcgct catctcggct    1860
cgtcgcacga ccgagtccaa cgacgtcctt tctctcgtga gtcaggcgct catcacactc    1920
gcgaacagaa gctgacgcac tcggtctcgc agctcctcgc cacccacctc tactgcgttc    1980
tccaagccat cgacttgcgc gcgatcgagt tcgagttcaa gaagcagttc ggcccagcca    2040
```

-continued

```
tcgtctcgct catcgaccag cactttggct ccgccatgac cggctcgaac ctgcgcgacg    2100
agctcgtcga aaggtgaac aagacgctcg ccaagcgcct cgagcagacc aactcgtacg    2160
acctcgtccc gcgctggcac gacgccttct ccttcgccgc cggcaccgtc gtcgaggtcc    2220
tctcgtcgac gtcgctctcg ctcgccgccg tcaacgcctg gaaggtcgcc gccgccgagt    2280
cggccatctc gctcacccgc caagtccgcg agaccttctg gtccgccgcg tcgacctcgt    2340
cgcccgcgct ctcgtacctc tcgccgcgca ctcagatcct ctacgccttc gtccgcgagg    2400
agcttggcgt caaggcccgc cgcggagacg tcttcctcgg caagcaagag gtgacgatcg    2460
gctcgaacgt ctccaagatc tacgaggcca tcaagtcggg caggatcaac aacgtcctcc    2520
tcaagatgct cgcttagaca ctcttcccac tctcgcatcc cttccatacc ctatcccgcc    2580
tgcacttctt aggactcgct tcttgtcgga ctcggatctc gcatcgcttc tttcgttctt    2640
ggctgcctct ctagaccgtg tcggtattac ctcgagattg tgaatacaag cagtacccat    2700
cca                                                                 2703
```

<210> SEQ ID NO 2
<211> LENGTH: 716
<212> TYPE: PRT
<213> ORGANISM: Rhodotorula glutinis

<400> SEQUENCE: 2

```
Met Ala Pro Ser Leu Asp Ser Ile Ser His Ser Phe Ala Asn Gly Val
  1               5                  10                  15

Ala Ser Ala Lys Gln Ala Val Asn Gly Ala Ser Thr Asn Leu Ala Val
                 20                  25                  30

Ala Gly Ser His Leu Pro Thr Thr Gln Val Thr Gln Val Asp Ile Val
             35                  40                  45

Glu Lys Met Leu Ala Ala Pro Thr Asp Ser Thr Leu Glu Leu Asp Gly
         50                  55                  60

Tyr Ser Leu Asn Leu Gly Asp Val Val Ser Ala Ala Arg Lys Gly Arg
 65                  70                  75                  80

Pro Val Arg Val Lys Asp Ser Asp Glu Ile Arg Ser Lys Ile Asp Lys
                 85                  90                  95

Ser Val Glu Phe Leu Arg Ser Gln Leu Ser Met Ser Val Tyr Gly Val
                100                 105                 110

Thr Thr Gly Phe Gly Gly Ser Ala Asp Thr Arg Thr Glu Asp Ala Ile
            115                 120                 125

Ser Leu Gln Lys Ala Leu Leu Glu His Gln Leu Cys Gly Val Leu Pro
        130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
```

-continued

```
                245                 250                 255
Pro Val Leu Gly Pro Lys Glu Gly Leu Gly Leu Val Asn Gly Thr
            260                 265                 270
Ala Val Ser Ala Ser Met Ala Thr Leu Ala Leu His Asp Ala His Met
        275                 280                 285
Leu Ser Leu Leu Ser Gln Ser Leu Thr Ala Met Thr Val Glu Ala Met
    290                 295                 300
Val Gly His Ala Gly Ser Phe His Pro Phe Leu His Asp Val Thr Arg
305                 310                 315                 320
Pro His Pro Thr Gln Ile Glu Val Ala Gly Asn Ile Arg Lys Leu Leu
                325                 330                 335
Glu Gly Ser Arg Phe Ala Val His His Glu Glu Val Lys Val Lys
            340                 345                 350
Asp Asp Glu Gly Ile Leu Arg Gln Asp Arg Tyr Pro Leu Arg Thr Ser
        355                 360                 365
Pro Gln Trp Leu Gly Pro Leu Val Ser Asp Leu Ile His Ala His Ala
    370                 375                 380
Val Leu Thr Ile Glu Ala Gly Gln Ser Thr Thr Asp Asn Pro Leu Ile
385                 390                 395                 400
Asp Val Glu Asn Lys Thr Ser His His Gly Gly Asn Phe Gln Ala Ala
                405                 410                 415
Ala Val Ala Asn Thr Met Glu Lys Thr Arg Leu Gly Leu Ala Gln Ile
            420                 425                 430
Gly Lys Leu Asn Phe Thr Gln Leu Thr Glu Met Leu Asn Ala Gly Met
        435                 440                 445
Asn Arg Gly Leu Pro Ser Cys Leu Ala Ala Glu Asp Pro Ser Leu Ser
    450                 455                 460
Tyr His Cys Lys Gly Leu Asp Ile Ala Ala Ala Tyr Thr Ser Glu
465                 470                 475                 480
Leu Gly His Leu Ala Asn Pro Val Thr Thr His Val Gln Pro Ala Glu
                485                 490                 495
Met Ala Asn Gln Ala Val Asn Ser Leu Ala Leu Ile Ser Ala Arg Arg
            500                 505                 510
Thr Thr Glu Ser Asn Asp Val Leu Ser Leu Leu Ala Thr His Leu
        515                 520                 525
Tyr Cys Val Leu Gln Ala Ile Asp Leu Arg Ala Ile Glu Phe Glu Phe
    530                 535                 540
Lys Lys Gln Phe Gly Pro Ala Ile Val Ser Leu Ile Asp Gln His Phe
545                 550                 555                 560
Gly Ser Ala Met Thr Gly Ser Asn Leu Arg Asp Glu Leu Val Glu Lys
                565                 570                 575
Val Asn Lys Thr Leu Ala Lys Arg Leu Glu Gln Thr Asn Ser Tyr Asp
            580                 585                 590
Leu Val Pro Arg Trp His Asp Ala Phe Ser Phe Ala Ala Gly Thr Val
        595                 600                 605
Val Glu Val Leu Ser Ser Thr Ser Leu Ser Leu Ala Ala Val Asn Ala
    610                 615                 620
Trp Lys Val Ala Ala Glu Ser Ala Ile Ser Leu Thr Arg Gln Val
625                 630                 635                 640
Arg Glu Thr Phe Trp Ser Ala Ala Ser Thr Ser Ser Pro Ala Leu Ser
                645                 650                 655
Tyr Leu Ser Pro Arg Thr Gln Ile Leu Tyr Ala Phe Val Arg Glu Glu
            660                 665                 670
```

```
Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
        690                 695                 700

Gly Arg Ile Asn Asn Val Leu Leu Lys Met Leu Ala
705                 710                 715

<210> SEQ ID NO 3
<211> LENGTH: 535
<212> TYPE: DNA
<213> ORGANISM: Lactobacillus plantarum

<400> SEQUENCE: 3
atgacaaaaa cttttaaaac acttgatgac tttctcggca cacactttat ctacacttat      60
gataacggct gggaatacga gtggtacgcc aagaacgacc acaccgttga ttaccgaatc     120
cacggtggga tggttgccgg tcgttgggtc actgatcaaa aagctgacat cgtcatgttg     180
accgaaggca tttacaaaat ttcttggact gaaccaactg ggactgacgt tgcactagac     240
ttcatgccca atgagaagaa actacacggt acgattttct tcccaaagtg ggttgaagaa     300
caccctgaaa ttacggtcac ttaccaaaac gaacacatcg atttaatgga acagtctcgt     360
gaaaagtatg ccacttatcc aaaactagtt gtacccgaat tgccaatata tacttacatg     420
ggcgagggcc aaaacaatga agatgtaatc agtgaagcac ttacaaaga aatgccgaat      480 gatattcgca acggcaagta cttgatcaaa actaccatcg tttaaataag taatg          535

<210> SEQ ID NO 4
<211> LENGTH: 174
<212> TYPE: PRT
<213> ORGANISM: Lactobacillus plantarum

<400> SEQUENCE: 4

Met Thr Lys Thr Phe Lys Thr Leu Asp Asp Phe Leu Gly Thr His Phe
1               5                   10                  15

Ile Tyr Thr Tyr Asp Asn Gly Trp Glu Tyr Glu Trp Tyr Ala Lys Asn
            20                  25                  30

Asp His Thr Val Asp Tyr Arg Ile His Gly Gly Met Val Ala Gly Arg
        35                  40                  45

Trp Val Thr Asp Gln Lys Ala Asp Ile Val Met Leu Thr Glu Gly Ile
    50                  55                  60

Tyr Lys Ile Ser Trp Thr Glu Pro Thr Gly Thr Asp Val Ala Leu Asp
65                  70                  75                  80

Phe Met Pro Asn Glu Lys Lys Leu His Gly Thr Ile Phe Phe Pro Lys
                85                  90                  95

Trp Val Glu Glu His Pro Glu Ile Thr Val Thr Tyr Gln Asn Glu His
            100                 105                 110

Ile Asp Leu Met Glu Gln Ser Arg Glu Lys Tyr Ala Thr Tyr Pro Lys
        115                 120                 125

Leu Val Val Pro Glu Phe Ala Asn Ile Thr Tyr Met Gly Glu Gly Gln
    130                 135                 140

Asn Asn Glu Asp Val Ile Ser Glu Ala Pro Tyr Lys Glu Met Pro Asn
145                 150                 155                 160

Asp Ile Arg Asn Gly Lys Tyr Leu Ile Lys Thr Thr Ile Val
                165                 170

<210> SEQ ID NO 5
```

<211> LENGTH: 486
<212> TYPE: DNA
<213> ORGANISM: Bacillus subtilis

<400> SEQUENCE: 5

```
atggaaaact ttatcggaag ccacatgatt tatacgtatg aaaacggatg ggaatacgag    60
atttatatta aaaacgacca tacaattgat tatagaattc atagcggaat ggttgccgga   120
cgctgggttc gagatcagga agtgaatatt gtcaaactga cagaaggcgt atataaagtg   180
tcttggacag agccgactgg cacggatgtt tcattaaact ttatgccaaa tgaaaaacgc   240
atgcatggca ttattttctt cccgaaatgg gtgcatgaac atcctgaaat tacggtttgc   300
taccaaaatg accacattga tttgatgaaa gaatcccgcg aaaaatatga acgtatcca    360
aaatacgttg tacctgaatt tgcgaaaatt acatttctga aaaatgaagg agtcgacaac   420
gaagaagtga tttcgaaggc tccttatgag ggaatgacag acgatattcg cgcgggaaga   480
ttataa                                                              486
```

<210> SEQ ID NO 6
<211> LENGTH: 161
<212> TYPE: PRT
<213> ORGANISM: Bacillus subtilis

<400> SEQUENCE: 6

```
Met Glu Asn Phe Ile Gly Ser His Met Ile Tyr Thr Tyr Glu Asn Gly
1               5                   10                  15
Trp Glu Tyr Glu Ile Tyr Ile Lys Asn Asp His Thr Ile Asp Tyr Arg
            20                  25                  30
Ile His Ser Gly Met Val Ala Gly Arg Trp Val Arg Asp Gln Glu Val
        35                  40                  45
Asn Ile Val Lys Leu Thr Glu Gly Val Tyr Lys Val Ser Trp Thr Glu
    50                  55                  60
Pro Thr Gly Thr Asp Val Ser Leu Asn Phe Met Pro Asn Glu Lys Arg
65                  70                  75                  80
Met His Gly Ile Ile Phe Phe Pro Lys Trp Val His Glu His Pro Glu
                85                  90                  95
Ile Thr Val Cys Tyr Gln Asn Asp His Ile Asp Leu Met Lys Glu Ser
            100                 105                 110
Arg Glu Lys Tyr Glu Thr Tyr Pro Lys Tyr Val Val Pro Glu Phe Ala
        115                 120                 125
Glu Ile Thr Phe Leu Lys Asn Glu Gly Val Asp Asn Glu Glu Val Ile
    130                 135                 140
Ser Lys Ala Pro Tyr Glu Gly Met Thr Asp Asp Ile Arg Ala Gly Arg
145                 150                 155                 160
Leu
```

<210> SEQ ID NO 7
<211> LENGTH: 34
<212> TYPE: DNA
<213> ORGANISM: artificial sequence
<220> FEATURE:
<223> OTHER INFORMATION: Primer

<400> SEQUENCE: 7

```
atagtagaat tcatggcacc ctcgctcgac tcga                               34
```

<210> SEQ ID NO 8
<211> LENGTH: 29

```
<212> TYPE: DNA
<213> ORGANISM: artificial sequence
<220> FEATURE:
<223> OTHER INFORMATION: Primer

<400> SEQUENCE: 8
gagagactgc agagaggcag ccaagaacg                                    29

<210> SEQ ID NO 9
<211> LENGTH: 18
<212> TYPE: DNA
<213> ORGANISM: artificial sequence
<220> FEATURE:
<223> OTHER INFORMATION: Primer

<400> SEQUENCE: 9
ggtaattcat atgacaaa                                                18

<210> SEQ ID NO 10
<211> LENGTH: 21
<212> TYPE: DNA
<213> ORGANISM: artificial sequence
<220> FEATURE:
<223> OTHER INFORMATION: Primer

<400> SEQUENCE: 10
tcacgtgaaa cattacttat t                                            21

<210> SEQ ID NO 11
<211> LENGTH: 19
<212> TYPE: DNA
<213> ORGANISM: artificial sequence
<220> FEATURE:
<223> OTHER INFORMATION: Primer

<400> SEQUENCE: 11
gtgtgtcata tggaaaact                                               19

<210> SEQ ID NO 12
<211> LENGTH: 19
<212> TYPE: DNA
<213> ORGANISM: artificial sequence
<220> FEATURE:
<223> OTHER INFORMATION: Primer

<400> SEQUENCE: 12
tcgcgggaat tgtgatggt                                               19

<210> SEQ ID NO 13
<211> LENGTH: 716
<212> TYPE: PRT
<213> ORGANISM: artificial sequence
<220> FEATURE:
<223> OTHER INFORMATION: Mutant from Rhodotorula glutinis
<220> FEATURE:
<221> NAME/KEY: MISC_FEATURE
<222> LOCATION: (126)..(126)
<223> OTHER INFORMATION: Xaa= Gly, Ser, Ala, or Thr
<220> FEATURE:
<221> NAME/KEY: MISC_FEATURE
<222> LOCATION: (138)..(138)
<223> OTHER INFORMATION: Xaa= Leu, Met, Ile, Val, or Cys
<220> FEATURE:
<221> NAME/KEY: MISC_FEATURE
<222> LOCATION: (149)..(149)
<223> OTHER INFORMATION: Xaa= Pro,  Ala, Ser, Thr, or Gly
<220> FEATURE:
<221> NAME/KEY: MISC_FEATURE
<222> LOCATION: (181)..(181)
```

```
<223> OTHER INFORMATION: Xaa= Pro, Ala, Ser, Thr, or Gly
<220> FEATURE:
<221> NAME/KEY: MISC_FEATURE
<222> LOCATION: (198)..(198)
<223> OTHER INFORMATION: Xaa= Asp, Asn, Glu, or Gln
<220> FEATURE:
<221> NAME/KEY: MISC_FEATURE
<222> LOCATION: (202)..(202)
<223> OTHER INFORMATION: Xaa= Val, Met, Leu, or Cys
<220> FEATURE:
<221> NAME/KEY: MISC_FEATURE
<222> LOCATION: (235)..(235)
<223> OTHER INFORMATION: Xaa= Ala, Gly, Ser, Thr, or Pro
<220> FEATURE:
<221> NAME/KEY: MISC_FEATURE
<222> LOCATION: (502)..(502)
<223> OTHER INFORMATION: Xaa= Gly, Ala, Ser, Thr, or Pro
<220> FEATURE:
<221> NAME/KEY: MISC_FEATURE
<222> LOCATION: (540)..(540)
<223> OTHER INFORMATION: Xaa= Thr, Ala, Ser, Pro, or Gly

<400> SEQUENCE: 13

Met Ala Pro Ser Leu Asp Ser Ile Ser His Ser Phe Ala Asn Gly Val
 1               5                  10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
 50                  55                  60

Tyr Ser Leu Asn Leu Gly Asp Val Val Ser Ala Ala Arg Lys Gly Arg
 65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Xaa Ala Ile
        115                 120                 125

Ser Leu Gln Lys Ala Leu Leu Glu His Xaa Leu Cys Gly Val Leu Pro
130                 135                 140

Ser Ser Phe Asp Xaa Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Xaa Ala Val Arg Leu Val Val Leu Glu Ala Leu Thr
            180                 185                 190

Asn Phe Leu Asn His Xaa Ile Thr Pro Xaa Val Pro Leu Arg Gly Thr
        195                 200                 205

Ile Ser Ala Ser Gly Asp Leu Ser Pro Leu Ser Tyr Ile Ala Ala Ala
210                 215                 220

Ile Ser Gly His Pro Asp Ser Lys Val His Xaa Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
```

-continued

```
                290                 295                 300
Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Val Lys Val Lys
                340                 345                 350

Asp Asp Glu Gly Ile Leu Arg Gln Asp Arg Tyr Pro Leu Arg Thr Ser
                355                 360                 365

Pro Gln Trp Leu Gly Pro Leu Val Ser Asp Leu Ile His Ala His Ala
370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
                420                 425                 430

Gly Lys Leu Asn Phe Thr Gln Leu Thr Glu Met Leu Asn Ala Gly Met
                435                 440                 445

Asn Arg Gly Leu Pro Ser Cys Leu Ala Ala Glu Asp Pro Ser Leu Ser
                450                 455                 460

Tyr His Cys Lys Gly Leu Asp Ile Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Xaa Asn Ser Leu Ala Leu Ile Ser Ala Arg Arg
                500                 505                 510

Thr Thr Glu Ser Asn Asp Val Leu Ser Leu Leu Ala Thr His Leu
                515                 520                 525

Tyr Cys Val Leu Gln Ala Ile Asp Leu Arg Ala Ile Glu Phe Glu Phe
                530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
                580                 585                 590

Leu Val Pro Arg Trp His Asp Ala Phe Ser Phe Ala Ala Gly Thr Val
                595                 600                 605

Val Glu Val Leu Ser Ser Thr Ser Leu Ser Leu Ala Ala Val Asn Ala
610                 615                 620

Trp Lys Val Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
                660                 665                 670

Leu Gly Val Lys Ala Arg Arg Gly Asp Val Phe Leu Gly Lys Gln Glu
                675                 680                 685

Val Thr Ile Gly Ser Asn Val Ser Lys Ile Tyr Glu Ala Ile Lys Ser
                690                 695                 700

Gly Arg Ile Asn Asn Val Leu Leu Lys Met Leu Ala
705                 710                 715
```

-continued

```
<210> SEQ ID NO 14
<211> LENGTH: 716
<212> TYPE: PRT
<213> ORGANISM: artificial sequence
<220> FEATURE:
<223> OTHER INFORMATION: Mutant from Rhodotorula glutinis
<220> FEATURE:
<221> NAME/KEY: MISC_FEATURE
<222> LOCATION: (126)..(126)
<223> OTHER INFORMATION: Xaa= Gly, Ala, Ser, or Thr
<220> FEATURE:
<221> NAME/KEY: MISC_FEATURE
<222> LOCATION: (138)..(138)
<223> OTHER INFORMATION: Xaa= Leu, Met, Ile, Val, or Cys
<220> FEATURE:
<221> NAME/KEY: MISC_FEATURE
<222> LOCATION: (540)..(540)
<223> OTHER INFORMATION: Xaa= Thr, Ala, Ser, Pro, or Gly

<400> SEQUENCE: 14

Met Ala Pro Ser Leu Asp Ser Ile Ser His Ser Phe Ala Asn Gly Val
  1               5                  10                  15

Ala Ser Ala Lys Gln Ala Val Asn Gly Ala Ser Thr Asn Leu Ala Val
             20                  25                  30

Ala Gly Ser His Leu Pro Thr Thr Gln Val Thr Gln Val Asp Ile Val
         35                  40                  45

Glu Lys Met Leu Ala Ala Pro Thr Asp Ser Thr Leu Glu Leu Asp Gly
     50                  55                  60

Tyr Ser Leu Asn Leu Gly Asp Val Val Ser Ala Arg Lys Gly Arg
 65                  70                  75                  80

Pro Val Arg Val Lys Asp Ser Asp Glu Ile Arg Ser Lys Ile Asp Lys
                 85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Xaa Ala Ile
        115                 120                 125

Ser Leu Gln Lys Ala Leu Leu Glu His Xaa Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
    290                 295                 300
```

```
Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
            325                 330                 335

Glu Gly Ser Arg Phe Ala Val His His Glu Glu Val Lys Val Lys
        340                 345                 350

Asp Asp Glu Gly Ile Leu Arg Gln Asp Arg Tyr Pro Leu Arg Thr Ser
            355                 360                 365

Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Asn Phe Gln Ala Ala
            405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
        435                 440                 445

Asn Arg Gly Leu Pro Ser Cys Leu Ala Ala Glu Asp Pro Ser Leu Ser
    450                 455                 460

Tyr His Cys Lys Gly Leu Asp Ile Ala Ala Ala Tyr Thr Ser Glu
465                 470                 475                 480

Leu Gly His Leu Ala Asn Pro Val Thr Thr His Val Gln Pro Ala Glu
            485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Ala Thr His Leu
        515                 520                 525

Tyr Cys Val Leu Gln Ala Ile Asp Leu Arg Ala Xaa Glu Phe Glu Phe
530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
            565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
610                 615                 620

Trp Lys Val Ala Ala Glu Ser Ala Ile Ser Leu Thr Arg Gln Val
625                 630                 635                 640

Arg Glu Thr Phe Trp Ser Ala Ser Thr Ser Ser Pro Ala Leu Ser
            645                 650                 655

Tyr Leu Ser Pro Arg Thr Gln Ile Leu Tyr Ala Phe Val Arg Glu Glu
        660                 665                 670

Leu Gly Val Lys Ala Arg Arg Gly Asp Val Phe Leu Gly Lys Gln Glu
675                 680                 685

Val Thr Ile Gly Ser Asn Val Ser Lys Ile Tyr Glu Ala Ile Lys Ser
        690                 695                 700

Gly Arg Ile Asn Asn Val Leu Leu Lys Met Leu Ala
705                 710                 715
```

```
<210> SEQ ID NO 15
<211> LENGTH: 716
<212> TYPE: PRT
<213> ORGANISM: artificial sequence
<220> FEATURE:
<223> OTHER INFORMATION: Mutant from Rhodotorula glutinis
<220> FEATURE:
<221> NAME/KEY: MISC_FEATURE
<222> LOCATION: (198)..(198)
<223> OTHER INFORMATION: Xaa= Asp, Asn, Glu, or Gln
<220> FEATURE:
<221> NAME/KEY: MISC_FEATURE
<222> LOCATION: (540)..(540)
<223> OTHER INFORMATION: Xaa= Thr, Ala, Ser, Pro, or Gly

<400> SEQUENCE: 15
```

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Xaa Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu

```
                         325                 330                 335
Glu Gly Ser Arg Phe Ala Val His His Glu Glu Val Lys Val Lys
                340                 345                 350
Asp Asp Glu Gly Ile Leu Arg Gln Asp Arg Tyr Pro Leu Arg Thr Ser
            355                 360                 365
Pro Gln Trp Leu Gly Pro Leu Val Ser Asp Leu Ile His Ala His Ala
        370                 375                 380
Val Leu Thr Ile Glu Ala Gly Gln Ser Thr Thr Asp Asn Pro Leu Ile
385                 390                 395                 400
Asp Val Glu Asn Lys Thr Ser His His Gly Gly Asn Phe Gln Ala Ala
                405                 410                 415
Ala Val Ala Asn Thr Met Glu Lys Thr Arg Leu Gly Leu Ala Gln Ile
                420                 425                 430
Gly Lys Leu Asn Phe Thr Gln Leu Thr Glu Met Leu Asn Ala Gly Met
            435                 440                 445
Asn Arg Gly Leu Pro Ser Cys Leu Ala Ala Glu Asp Pro Ser Leu Ser
        450                 455                 460
Tyr His Cys Lys Gly Leu Asp Ile Ala Ala Ala Tyr Thr Ser Glu
465                 470                 475                 480
Leu Gly His Leu Ala Asn Pro Val Thr Thr His Val Gln Pro Ala Glu
                485                 490                 495
Met Ala Asn Gln Ala Val Asn Ser Leu Ala Leu Ile Ser Ala Arg Arg
                500                 505                 510
Thr Thr Glu Ser Asn Asp Val Leu Ser Leu Leu Ala Thr His Leu
            515                 520                 525
Tyr Cys Val Leu Gln Ala Ile Asp Leu Arg Ala Xaa Glu Phe Glu Phe
        530                 535                 540
Lys Lys Gln Phe Gly Pro Ala Ile Val Ser Leu Ile Asp Gln His Phe
545                 550                 555                 560
Gly Ser Ala Met Thr Gly Ser Asn Leu Arg Asp Glu Leu Val Glu Lys
                565                 570                 575
Val Asn Lys Thr Leu Ala Lys Arg Leu Glu Gln Thr Asn Ser Tyr Asp
                580                 585                 590
Leu Val Pro Arg Trp His Asp Ala Phe Ser Phe Ala Ala Gly Thr Val
            595                 600                 605
Val Glu Val Leu Ser Ser Thr Ser Leu Ser Leu Ala Ala Val Asn Ala
        610                 615                 620
Trp Lys Val Ala Ala Ala Glu Ser Ala Ile Ser Leu Thr Arg Gln Val
625                 630                 635                 640
Arg Glu Thr Phe Trp Ser Ala Ala Ser Thr Ser Ser Pro Ala Leu Ser
                645                 650                 655
Tyr Leu Ser Pro Arg Thr Gln Ile Leu Tyr Ala Phe Val Arg Glu Glu
                660                 665                 670
Leu Gly Val Lys Ala Arg Arg Gly Asp Val Phe Leu Gly Lys Gln Glu
            675                 680                 685
Val Thr Ile Gly Ser Asn Val Ser Lys Ile Tyr Glu Ala Ile Lys Ser
        690                 695                 700
Gly Arg Ile Asn Asn Val Leu Leu Lys Met Leu Ala
705                 710                 715

<210> SEQ ID NO 16
<211> LENGTH: 716
<212> TYPE: PRT
<213> ORGANISM: artificial sequence
```

-continued

```
<220> FEATURE:
<223> OTHER INFORMATION: Mutant from Rhodotorula glutinis
<220> FEATURE:
<221> NAME/KEY: MISC_FEATURE
<222> LOCATION: (181)..(181)
<223> OTHER INFORMATION: Xaa= Pro, Ala, Ser, Thr, or Gly
<220> FEATURE:
<221> NAME/KEY: MISC_FEATURE
<222> LOCATION: (235)..(235)
<223> OTHER INFORMATION: Xaa= Ala, Gly, Ser, Thr, or Pro
<220> FEATURE:
<221> NAME/KEY: MISC_FEATURE
<222> LOCATION: (540)..(540)
<223> OTHER INFORMATION: Xaa= Thr, Ala, Ser, Pro, or Gly

<400> SEQUENCE: 16
```

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
50                  55                  60

Tyr Ser Leu Asn Leu Gly Asp Val Val Ser Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Xaa Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
210                 215                 220

Ile Ser Gly His Pro Asp Ser Lys Val His Xaa Val His Glu Gly Lys
225                 230                 235                 240

Glu Lys Ile Leu Tyr Ala Arg Glu Ala Met Ala Leu Phe Asn Leu Glu
                245                 250                 255

Pro Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

```
Glu Gly Ser Arg Phe Ala Val His His Glu Glu Val Lys Val Lys
            340                 345                 350

Asp Asp Glu Gly Ile Leu Arg Gln Asp Arg Tyr Pro Leu Arg Thr Ser
            355                 360                 365

Pro Gln Trp Leu Gly Pro Leu Val Ser Asp Leu Ile His Ala His Ala
            370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
            405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
            435                 440                 445

Asn Arg Gly Leu Pro Ser Cys Leu Ala Ala Glu Asp Pro Ser Leu Ser
            450                 455                 460

Tyr His Cys Lys Gly Leu Asp Ile Ala Ala Ala Tyr Thr Ser Glu
465                 470                 475                 480

Leu Gly His Leu Ala Asn Pro Val Thr Thr His Val Gln Pro Ala Glu
                    485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Leu Ala Thr His Leu
            515                 520                 525

Tyr Cys Val Leu Gln Ala Ile Asp Leu Arg Ala Xaa Glu Phe Glu Phe
530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                    565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
            595                 600                 605

Val Glu Val Leu Ser Ser Thr Ser Leu Ser Leu Ala Ala Val Asn Ala
            610                 615                 620

Trp Lys Val Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                    645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
            675                 680                 685

Val Thr Ile Gly Ser Asn Val Ser Lys Ile Tyr Glu Ala Ile Lys Ser
            690                 695                 700

Gly Arg Ile Asn Asn Val Leu Leu Lys Met Leu Ala
705                 710                 715

<210> SEQ ID NO 17
<211> LENGTH: 716
<212> TYPE: PRT
<213> ORGANISM: artificial sequence
<220> FEATURE:
```

```
<223> OTHER INFORMATION: Mutant from Rhodotorula glutinis
<220> FEATURE:
<221> NAME/KEY: MISC_FEATURE
<222> LOCATION: (149)..(149)
<223> OTHER INFORMATION: Xaa= Pro, Ala, Ser, Thr, or Gly
<220> FEATURE:
<221> NAME/KEY: MISC_FEATURE
<222> LOCATION: (202)..(202)
<223> OTHER INFORMATION: Xaa=Val, Met, Leu, or Cys
<220> FEATURE:
<221> NAME/KEY: MISC_FEATURE
<222> LOCATION: (540)..(540)
<223> OTHER INFORMATION: Xaa= Thr, Ala, Ser, Pro, or Gly

<400> SEQUENCE: 17
```

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
            35                  40                  45

Glu Lys Met Leu Ala Ala Pro Thr Asp Ser Thr Leu Glu Leu Asp Gly
50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
            115                 120                 125

Ser Leu Gln Lys Ala Leu Leu Glu His Gln Leu Cys Gly Val Leu Pro
130                 135                 140

Ser Ser Phe Asp Xaa Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Xaa Val Pro Leu Arg Gly Thr
            195                 200                 205

Ile Ser Ala Ser Gly Asp Leu Ser Pro Leu Ser Tyr Ile Ala Ala Ala
210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
            275                 280                 285

Leu Ser Leu Leu Ser Gln Ser Leu Thr Ala Met Thr Val Glu Ala Met
290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

```
Glu Gly Ser Arg Phe Ala Val His His Glu Glu Val Lys Val Lys
            340                 345                 350

Asp Asp Glu Gly Ile Leu Arg Gln Asp Arg Tyr Pro Leu Arg Thr Ser
                355                 360                 365

Pro Gln Trp Leu Gly Pro Leu Val Ser Asp Leu Ile His Ala His Ala
        370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
                420                 425                 430

Gly Lys Leu Asn Phe Thr Gln Leu Thr Glu Met Leu Asn Ala Gly Met
            435                 440                 445

Asn Arg Gly Leu Pro Ser Cys Leu Ala Ala Glu Asp Pro Ser Leu Ser
450                 455                 460

Tyr His Cys Lys Gly Leu Asp Ile Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
                500                 505                 510

Thr Thr Glu Ser Asn Asp Val Leu Ser Leu Leu Ala Thr His Leu
            515                 520                 525

Tyr Cys Val Leu Gln Ala Ile Asp Leu Arg Ala Xaa Glu Phe Glu Phe
530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
                580                 585                 590

Leu Val Pro Arg Trp His Asp Ala Phe Ser Phe Ala Ala Gly Thr Val
            595                 600                 605

Val Glu Val Leu Ser Ser Thr Ser Leu Ser Leu Ala Ala Val Asn Ala
            610                 615                 620

Trp Lys Val Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
                660                 665                 670

Leu Gly Val Lys Ala Arg Arg Gly Asp Val Phe Leu Gly Lys Gln Glu
            675                 680                 685

Val Thr Ile Gly Ser Asn Val Ser Lys Ile Tyr Glu Ala Ile Lys Ser
            690                 695                 700

Gly Arg Ile Asn Asn Val Leu Leu Lys Met Leu Ala
705                 710                 715
```

<210> SEQ ID NO 18
<211> LENGTH: 716
<212> TYPE: PRT
<213> ORGANISM: artificial sequence
<220> FEATURE:
<223> OTHER INFORMATION: Mutant from Rhodotorula glutinis

```
<220> FEATURE:
<221> NAME/KEY: MISC_FEATURE
<222> LOCATION: (502)..(502)
<223> OTHER INFORMATION: Xaa= Gly, Ala, Ser, Thr, or Pro
<220> FEATURE:
<221> NAME/KEY: MISC_FEATURE
<222> LOCATION: (540)..(540)
<223> OTHER INFORMATION: Xaa= Thr, Ala, Ser, Pro, or Gly

<400> SEQUENCE: 18
```

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Val Lys Val Lys
            340                 345                 350

Asp Asp Glu Gly Ile Leu Arg Gln Asp Arg Tyr Pro Leu Arg Thr Ser
        355                 360                 365

-continued

```
Pro Gln Trp Leu Gly Pro Leu Val Ser Asp Leu Ile His Ala His Ala
    370                 375                 380
Val Leu Thr Ile Glu Ala Gly Gln Ser Thr Thr Asp Asn Pro Leu Ile
385                 390                 395                 400
Asp Val Glu Asn Lys Thr Ser His His Gly Gly Asn Phe Gln Ala Ala
                405                 410                 415
Ala Val Ala Asn Thr Met Glu Lys Thr Arg Leu Gly Leu Ala Gln Ile
                420                 425                 430
Gly Lys Leu Asn Phe Thr Gln Leu Thr Glu Met Leu Asn Ala Gly Met
            435                 440                 445
Asn Arg Gly Leu Pro Ser Cys Leu Ala Ala Glu Asp Pro Ser Leu Ser
    450                 455                 460
Tyr His Cys Lys Gly Leu Asp Ile Ala Ala Ala Tyr Thr Ser Glu
465                 470                 475                 480
Leu Gly His Leu Ala Asn Pro Val Thr Thr His Val Gln Pro Ala Glu
                485                 490                 495
Met Ala Asn Gln Ala Xaa Asn Ser Leu Ala Leu Ile Ser Ala Arg Arg
                500                 505                 510
Thr Thr Glu Ser Asn Asp Val Leu Ser Leu Leu Ala Thr His Leu
            515                 520                 525
Tyr Cys Val Leu Gln Ala Ile Asp Leu Arg Ala Xaa Glu Phe Glu Phe
    530                 535                 540
Lys Lys Gln Phe Gly Pro Ala Ile Val Ser Leu Ile Asp Gln His Phe
545                 550                 555                 560
Gly Ser Ala Met Thr Gly Ser Asn Leu Arg Asp Glu Leu Val Glu Lys
                565                 570                 575
Val Asn Lys Thr Leu Ala Lys Arg Leu Glu Gln Thr Asn Ser Tyr Asp
            580                 585                 590
Leu Val Pro Arg Trp His Asp Ala Phe Ser Phe Ala Ala Gly Thr Val
    595                 600                 605
Val Glu Val Leu Ser Ser Thr Ser Leu Ser Leu Ala Ala Val Asn Ala
610                 615                 620
Trp Lys Val Ala Ala Ala Glu Ser Ala Ile Ser Leu Thr Arg Gln Val
625                 630                 635                 640
Arg Glu Thr Phe Trp Ser Ala Ala Ser Thr Ser Ser Pro Ala Leu Ser
                645                 650                 655
Tyr Leu Ser Pro Arg Thr Gln Ile Leu Tyr Ala Phe Val Arg Glu Glu
                660                 665                 670
Leu Gly Val Lys Ala Arg Arg Gly Asp Val Phe Leu Gly Lys Gln Glu
            675                 680                 685
Val Thr Ile Gly Ser Asn Val Ser Lys Ile Tyr Glu Ala Ile Lys Ser
    690                 695                 700
Gly Arg Ile Asn Asn Val Leu Leu Lys Met Leu Ala
705                 710                 715
```